United States Patent [19]

Mowbray et al.

[11] Patent Number: 6,086,879
[45] Date of Patent: Jul. 11, 2000

[54] ANTIBODY TO THE SYNCYTIOTROPHOBLAST ANTIGEN R80K AND USE THEREOF

[75] Inventors: James F. Mowbray, London, United Kingdom; Gerard C. P. Chaouat, Paris, France; Gholam R. Jalali, London, United Kingdom

[73] Assignee: Imperial College of Science Technology and Medicone, London, United Kingdom

[21] Appl. No.: 08/944,104

[22] Filed: Sep. 30, 1997

Related U.S. Application Data

[63] Continuation of application No. PCT/GB96/00781, Apr. 1, 1996.

[30] Foreign Application Priority Data

Mar. 31, 1995 [GB] United Kingdom .................... 9506646
Jun. 16, 1995 [GB] United Kingdom .................... 9512314

[51] Int. Cl.[7] .......................... A61K 39/395; C12N 5/20; G01N 33/53; C07K 16/28
[52] U.S. Cl. ....................... 424/172.1; 435/332; 435/810; 435/975; 530/387.1; 530/388.2; 530/389.1
[58] Field of Search ..................................... 435/332, 810, 435/975; 530/387.1, 388.2, 389.1; 424/172.1

[56] References Cited

PUBLICATIONS

The Journal of Immunology, vol. 141, No. 8, Oct. 15, 1988, Baltimore, MD, USA, pp. 2861–2868, L. Jaso–Friedmann et al.: "Characterization by monoclonal antibodies of a target cell antigen complex recognized by nonspecific cytotoxic cells".
Cellular Immunology, vol. 157, No. 2, Sep. 1994, New York, NY, USA, pp. 328–340, G. Chaouat: "Synergy of lipopolysaccaride and inflammatory cytokines in murine pregnancy: alloimmunization prevents abortion but does not affect the induction of preterm delivery".
Journal of Clinical and Laboratory Immunology, vol. 23 1987, Edinburgh, GB, pp. 63–69, M. Crainie et al.: "A new human trophoblast antigen isolated from immune complexes derived from placental blood and membranes.".
American Journal of Reproductive Immunology, vol. 33, No. 3, Mar. 1995, New York, NY, USA, pp. 213–220, G.Jalali et al.: "An 80–Kda syncytiotrophoblast alloantibody in term placenta.".

Voisin, G. A. et al, J. Reprod. Fert., Suppl.21 89–103, (1974).
Hai, B.B.L. et al, Cellular and Molecular Biology/Inserm, vol. 212:3–11 (1991).
Davies, M. et al, J. Reprod. Immunology, 7:285–297 (1985).
Pellegrino, M.A. et al, Clin. Immunology, 3:324–333 (1975).
Mittal, K.K. et al, Transplantation, vol. 6, No. 8:913–927 (1968).
Hayakawa, K. et al, J. Exp. Med. vol. 157:202–218 (1983).
Clark, D.A. et al, Cellular Immunology, 154:143–152 (1994).
Kinsky, R. et al, Cellular and Molecular Biology/Inserm, vol. 212:245–259 (1991).
Smith, N.C. et al, Nature, vol. 252:302–303 (1974).
McGuire, T.C. et al, Am. J. Vet. Res. 34:1299–1303 (1973).
Jalali, G.R. et al, Transplant. Proc., vol. 21, No. 1:572–574 (1989).
Chaouat, G. et al, Cellular and Molecular Biology/Inserm, vol. 212:91–100 (199 1).
Chaouat, G. et al, J. Reprod. Immunolgoy, 5:389–392 (1983).
Sulica, A. et al, J. Immunology, vol. 128, No. 3:1031–1036 (1982).
Chaouat, G. et al, J. Immunology, vol. 134, No. 3:1594–1598 (1985).
Jaso–Friedmann, L. et al, J. Immunoigy, vol. 141, No. 8, 2861–2868 (1988).
Van Rood, J.J. et al, Nature, 181:1735–1736 (1958).

*Primary Examiner*—Christina Y. Chan
*Assistant Examiner*—F. Pierre VanderVegt
*Attorney, Agent, or Firm*—Nixon & Vanderhye

[57] ABSTRACT

This invention relates to a method for suppressing the cytotoxic activity of mammalian Natural Killer (NK) cells, especially in women experiencing repeated miscarriages. An antibody which binds to an 80 kDa surface protein on the maternal surface of normal term human syncytiotrophoblast (R80K) was discovered. This antibody was also found to bind to Natural Killer (NK) target cells (K562) and inhibit NK killing of this human NK target cell line. A monoclonal antibody (BA11) was raised against K562 cells which was also directed against a monomorphic site on the R80K surface protein of placentae. BA11 was found both to inhibit the attachment of NK cells and killing of both target cells.

13 Claims, 19 Drawing Sheets

| SAMPLE | PROTEIN BINDING (cpm) | |
|---|---|---|
| V UNACIDIFIED MICROVESICLES | 1105 | ±230 |
| $V_a$ | 198 | ±88 |
| $V_a$ +ISOLOGOUS $Ab_e$ | 1010 | ±77 |
| $V_a$ +$Ab_e$ ABSORBED WITH TRYPTIC DIGEST OF THE SAME PLACENTA | 233 | ±44 |
| $V_a$ +$Ab_e$ ABSORBED WITH TRYPTIC DIGEST OF ANOTHER PLACENTA | 940 | ±41 |

| | $V_a^1$ | $V_a^2$ | $V_a^3$ | $V_a^4$ | $V_a^5$ | $V_a^6$ | $V_a^7$ | $V_a^8$ | $V_a^9$ | $V_a^{10}$ | $V_a^{11}$ | $V_a^{12}$ |
|---|---|---|---|---|---|---|---|---|---|---|---|---|
| $Ab_e^1$ | 1.0 | 0.5 | 0.0 | 0.0 | 0.1 | 0.4 | 1.3 | 0.4 | 0.1 | 0.0 | 0.0 | 0.1 |
| $Ab_e^2$ | 0.4 | 1.0 | 0.6 | 0.6 | 0.4 | 0.8 | 0.6 | 0.7 | 0.0 | 0.1 | 0.5 | 0.3 |
| $Ab_e^3$ | 1.2 | 0.6 | 1.0 | 0.1 | 1.2 | 0.4 | 0.6 | 0.4 | 0.0 | 1.0 | 0.0 | 0.4 |
| $Ab_e^4$ | 0.3 | 0.4 | 0.5 | 1.0 | .2 | 0.3 | 0.3 | 0.2 | 0.1 | 0.0 | 0.4 | 0.4 |
| $Ab_e^5$ | 0.3 | 0.3 | 0.2 | 0.0 | 1.0 | 0.0 | 0.2 | 0.2 | 0.0 | 0.4 | 0.1 | 0.3 |
| $Ab_e^6$ | 0.0 | 1.0 | 0.6 | 0.0 | 0.0 | 1.0 | 0.9 | 0.5 | 0.2 | 0.0 | 0.2 | 1.2 |
| $Ab_e^7$ | 0.0 | 0.1 | 0.1 | 0.1 | 0.2 | 0.4 | 1.0 | 0.3 | 0.1 | 0.1 | 0.1 | 0.1 |
| $Ab_e^8$ | 0.9 | 0.8 | 0.7 | 0.9 | 0.0 | 0.1 | 0.2 | 1.0 | 0.8 | 0.2 | 0.5 | 0.3 |
| $Ab_e^9$ | 0.3 | 0.0 | 0.9 | 1.0 | 0.6 | 0.3 | 0.9 | 0.5 | 1.0 | 0.2 | 0.5 | 1.2 |
| $Ab_e^{10}$ | 0.3 | 0.1 | 0.3 | 0.6 | 0.0 | 0.6 | 0.3 | 0.0 | 0.8 | 1.0 | 0.4 | .01 |
| $Ab_e^{11}$ | 0.9 | 0.2 | 0.2 | 0.0 | 1.2 | 0.4 | 0.1 | 0.0 | 0.3 | 0.0 | 1.0 | 0.0 |
| $Ab_e^{12}$ | 0.1 | 0.3 | 0.4 | 0.0 | 0.4 | 0.4 | 0.2 | 0.8 | 0.0 | 0.1 | 0.1 | 1.0 |

FIG. 19

| ANTIBODY | CELL 1 (% KILL) | CELL 2 (% KILL) | CELL 3 (% KILL) | CELL 4 (% KILL) |
|---|---|---|---|---|
| NEG CONTROL | 30 30 | 30 20 | 20 30 | 30 30 |
| POS CONTROL | 100 100 | 100 100 | 100 100 | 100 100 |
| 3 | 30 30 | 20 20 | 30 30 | 90 70 |
| 4 | 30 30 | 20 30 | 30 30 | 30 40 |
| 5 | 50 15 | 70 70 | 60 60 | 80 ns |
| 6 | 75 60 | 30 30 | 100 100 | 30 40 |
| 9 | ns 100 | 20 20 | 30 30 | 20 40 |
| 11 | 50 70 | 20 20 | 30 30 | 30 40 |
| 12 | 85 80 | 20 20 | 30 20 | 30 30 |
| 13 | 20 20 | 100 90 | 50 40 | 30 30 |
| 14 | 80 70 | 30 20 | 30 40 | 20 40 |
| 24 | 80 70 | 60 60 | 90 90 | ns 40 |
| 25 | 20 20 | 20 30 | 40 30 | ns 60 |
| 26 | 85 80 | 30 30 | 50 40 | 80 60 |
| 27 | 40 50 | 90 90 | 80 90 | 80 80 |
| 28 | 20 40 | 90 90 | 90 90 | 60 60 |

ANTIBODY TO THE SYNCYTIOTROPHOBLAST ANTIGEN R80K AND USE THEREOF

This is a continuation of PCT application No. PCT/GB96/00781, filed Apr. 1, 1996.

The present invention relates to a method for suppressing the cytotoxic activity of mammalian Natural Killer (NK) cells, especially in women experiencing repeated miscarriages.

The syncytiotrophoblast, the fetal cells in intimate contact with maternal circulation, has a number of unique properties which protect and nourish the fetus during gestation. The maternal surface has a microvillus border which increases enormously the surface area to allow for maximum transplacental transport. Below the transition temperature of the membrane, and in the absence of calcium ions, microvesicles break off with minimal shearing force (Smith et al., *Nature* 252 302–303 (1974)). This allows for the detailed study of this plasma membrane. In both human and horse placenta, IgG binds to this plasma membrane. Specifically, in humans, an IgG is bound to an Fc receptor and is actively transported from mother to fetus, but in the horse there is no transport of IgG (McGuire et al., *Am. J. Vet. Res.* 34 1299–1303 (1973)), and thus probably no Fc receptors.

We found previously that IgG which is not bound to Fc receptors is bound to an epitope on a polymorphic trophoblast antigen (Jalali et al., *Transplant Proc.* 81 572–574 (1989)). We also found that IgG bound to the Fc receptor is dissociated under mild acid conditions, but that when bound to the antigen it is removed from the trophoblast microvesicles only at pH 3. We further found the antigen in both horse and human varied from placenta to placenta in an apparently highly polymorphic way, and the IgG eluted in acid conditions would rebind specifically to the microvesicles from which it was removed, and to a small fraction of other placentae (Mowbray et al., *Clin. Immunol. Path.* 3 324–333 (1975)). We studied more than 700 human term placentae and 53 term horse placentae. All placentae were found to have IgG antibody bound to an 80 kDa surface protein derived from the maternal surface of normal term human syncytiotrophoblast (R80K). Under acid conditions the IgG antibodies can be dissociated from the microvesicles. In working only with human placentae, we found that placental IgG was bound both to a polymorphic protein and the Fc receptor (Jalali et al., *Transplant Proc.* 81 572–574 (1989)). The IgG bound to the Fc receptor is being actively transported to the fetus. As stated above, since there is no transport of IgG across the placenta in the horse (McGuire et al., *Am. J. Vet. Res.* 34 1299–1303 (1973)), and hence presumptively no Fc receptors, all the IgG in the horse is bound to alloantigen on the trophoblast, the equine analogue of the R80K in the human.

In both humans and horses the IgG antibody from placenta will reassociate with the microvesicles from which it was eluted. In humans, cross reaction with other treated vesicles were found in only 5 out of 30 (16.7%) and in horses in 18 out of 132 (13.6%) reactions. Thus in both species the antigen is highly polymorphic. Small variations in protein sequences are common, but antigenic variation to this degree is unusual. The paternal antigen is different from the maternal antigen (most of the time) and is thus capable of eliciting a maternal IgG antibody response. No term placenta has yet been found without the IgG antibody, although about 15% might be expected as the mother would have an identical antigen to the fetus preventing her from making an antibody response.

The mechanisms by which maternal immunity modifies her attack on trophoblasts by particular cellular mechanisms have been the subject of considerable controversy. A number of clear observations made by co-inventor Gerard Chaouat established the nature of the abortion/resorption mechanism in mice (Chaouat et al., INSERM/John Libbey Eurotext Ltd 212 91–100 (1991)). This work demonstrates in F1 matings between CBA and DBA2 mice, the mechanism which causes resorption of embryos in mice is based on natural killer cell activity (NK). The high resorption rate of CBA/DBA2 mice pregnancies can be prevented by the use of pentoxyfylline (which inhibits the release of Tumour Necrosis Factor (TNF) from stimulated macrophages), by use of a polyclonal rabbit anti-TNF antibody, or by depletion of asialo GM1 positive cells prior to the pregnancy. TNF is responsible for resorption of embryos in mice models. The TNF is probably acting more as an activator of the NK cells than as a mediator of NK killing at the target cell surface. More importantly, immunisation of the CBA females by spleen cells from the paternal strain prior to pregnancy, prevents high resorption rate (Chaouat et al., *J. Reproduct Immunology* 5 389–92 (1983)). Transfer of immune IgG from another mouse was found to be very effective in blocking TNF and NK mediated fetal loss. It has also been shown that resorption may be triggered within inbred strain matings by administration of endotoxin, but this is much more difficult to achieve in interstrain combinations (Chaouat et al., *J. Reproduct Immunology* 10: 179–83). The relative inefficiency of endotoxin in this situation may be related to the development of maternal alloimmunity to fetal alloantigens. In support of this are experiments which show immunization with allogenic lymphocytes protects against NK-mediated resorption of F1 embryos of interstrain matings (Chaouat et al., *J. Immunology* 134 1594–1598 (1985)). Because Natural Killer cell activity was an essential part of the resorption/abortion in pregnant CBA-DBA/2 mice, we were prompted to see if an antibody was available which would bind to an NK target molecule on the cell surface in both mice and in humans.

Another research group has attempted to show that the target protein required for NK/LAK attachment to the target cell surface was an 80 kDa protein, detectable on the standard human NK target K562 (Jaso-Friedmann et al., *J. Immunol.* 141 2861–2868 (1988)). They claimed a monoclonal antibody directed against a monomorphic determinant on the surface of YAK, the mouse standard NK target, and a fish parasitic worm. The antibody was able to inhibit NK killing of the target cell for each of these cells, as well as demonstrating its ability to prevent adherence by the NK cell to its target. However, the effects were extremely non-specific and never indicated the use of such antibodies against placenta nor suggested any potential use for the antibody.

It is well known in the art that the adhesion molecule of NK cells is the neuronal cell adhesion molecule (NCAM). This protein is highly glycosylated on NK cells, and prevents homoadhesion. The adhesion molecule on at least some target cells is the 80 kDa protein which we have called R80K. The evidence for this lies in our surprising discovery that IgG antibodies eluted from R80K will bind to K562, and prevent NK killing, in a dose dependent fashion (FIG. 1 and FIG. 15). It is also of great interest that this antibody which reacts with only about ten percent of allotypes of the protein, bound to one epitope and inhibited NK killing of the target cell, and a second antibody bound to another monomorphic determinant on K562 and also inhibited NK killing.

The majority of human placentae used in developing the present invention were derived from first pregnancies so that immunogenicity of this antigen is much higher than MHC antigens. In both human and murine pregnancies it is difficult to find MHC antibodies in first or second pregnancies (van Rood J. J., et al., *Nature* 181 1735 (1958) and (Voisin et al., *J. Reprod. Fertil. suppl.* 21 89–103 (1974)), but anti-R80K antibodies are found on all term human placentae. Central to the present invention, is our finding that most women with recurrent early pregnancy loss do not possess antibodies against the R80K antigen.

Studies on homozygous lymphoblastoid cell lines were made to investigate a possible HLA association. Eluted antibodies reacted with one, or at most two, of the B cell lines. Different eluates, both reacting with other cell lines, reacted together with one cell, so that at least one of the four lines has two detectable antigenic specificities present. These make an association between the R80K molecule and human MHC very unlikely.

The demonstration of a novel polymorphic antigenic system on human cells immediately leads to a search for a site for the gene(s) responsible. The size and single peptide nature of R80K makes homology with MHC Class I or Class II antigens unlikely. The studies which we have made in collaboration with BA Bradley in Bristol indicate there are no measurable linkage with HLA antigens (Table III). In families the segregation is separate from HLA, and studies using lymphoblastoid cell lines show lack of correlation between HLA antigens and the R80K antigenic polymorphism.

Hai et al., *Colloque version* 212 3–11 (1990) found that the complement modulating proteins which are in high concentration on this membrane explain why the antibody does not damage the syncytiotrophoblast, even though the membrane is bathed in human complement containing plasma. There have been several attempts to demonstrate NK or LAK killing of human cytotrophoblast, and reports that the cultured trophoblast is susceptible to attack by LAK cells suggest the bound antibody which is shed with the antigen on culture prevents attack on fresh cells.

In our work we have identified a highly polymorphic protein alloantigen present on the microvesicles prepared from human term placental syncytiotrophoblast. The alloantibodies eluted from the microvesicles show there is at least a limited distribution of the antigen on other cell types, in particular B lymphocytes and monocytes. The alloantigen is quite distinct from MHC, as shown by independent assortment of R80K and HLA alloantigen on HLA homozygous cultured human lymphoblastoid cell lines. In the horse, the alloantigen detected showed no association with the ELA antigens, using conventional serological techniques (D. Antzcak, personal communication). In addition, a single 80 kDa human chain is quite unlike the structure of MHC Class I or Class II antigens. R80K, unprotected by the antibody normally covering it, can be cleaved by trypsin to produce a soluble fragment which has the antigenic epitopes within it. Davies & Browne (*J. Reprod. Inmuunol.* 7 285–297 (1985)) claimed to find IgG and some IgM antibody in the serum of pregnant women directed against a syncytiotrophoblast antigen. They claimed that the IgG antibody was not polymorphic and reacted with most other placentae. This is clearly incorrect as the R80K is highly polymorphic as has already been described.

Similar results to that in the human have been found in horses in which species trophoblast microvesicles can be prepared as in the human (Mathias et al., Proc. 6th International Symposium on Equine Reproduction. pp47–48 (1994)). All these preparations contain IgG antibody bound to a similar protein on the plasma membrane surface, and again this is highly polymorphic. The antigenic R80K proteins which were used in developing our invention were saturated with IgG antibody in all term placentae studied. This implies two important things, not only is the R80K very immunogenic, since this is true of first pregnancies as well as later ones, but most importantly, the R80K antigen is covered with IgG antibody in successful pregnancies.

The experimental data presented in the examples demonstrate that antibody on syncytiotrophoblast plasma membrane microvesicles are attached to a highly polymorphic epitope on the R80K protein. Another group (Crainie and Stimson, *J. Clin. Immunol.* 23 63–69 (1987)) carried out a similar preparation of the antigen as that used by us in which IgG antibody was bound. The antigen was also found to weigh approximately 80 kDa. This group also failed to recognise that the epitope was polymorphic. This polymorphism of the antibody is of great importance. It is therefore an aspect of this invention to provide an IgG antibody which recognises and binds to NK target cells thus preventing NK killing of those cells and abortion of the fetus.

One of the examples described herein demonstrates that if the IgG antibody is removed from the microvesicles by acid dissociation, it will bind to other human cells that cross-react antigenically. Choosing those few eluates which were found to react with K562 cells, the standard target cell for human NK/LAK killing, inhibition of binding was effected by saturating the R80K sites on the K562 target cells. This inhibition was not observed with IgG eluates which did not bind to the K562 targets.

The above results strongly suggest that the same polymorphic epitope is present on the K562 as well as on the syncytiotrophoblast and this epitope is involved in the adherence and killing of K562 by natural killer cells. We then began searching for an additional epitope on the 80 kDa protein which did not show allopolymorphism, but could also block NK killing. We made several monoclonal antibodies against the R80K molecule of placental microvesicles, and determined that these were also inhibiting NK/LAK killing of K562 (Example 2). These monoclonals, and one in particular, BA11, strongly inhibit NK killing on target cells (FIGS. 2 and 3). Other Mabs against R80K were ineffective in preventing NK killing. Our studies show that BA11 binds to R80K obtained from several different placentae, unlike the IgG antibodies obtained by acid dissociation, which only bound to homologous R80K. Thus, although the alloantigenic epitope is highly polymorphic, the BA11 site is monomorphic. However, both types of antibodies may be used to inhibit NK/LAK activity on K562 target cells. The BA11 monoclonal antibody belongs to the IgM class of antibodies. Applicants have deposited their monoclonal antibody, BA11, at the European Collection of Animal Cell Cultures, Porton Down, Salisbury, Wiltshire SP4 OJG on Apr. 20, 1995 and assigned Depository Accession Number 95042013.

The universal prevalence of the IgG antibody in successful human and equine pregnancies arises due to a high degree of antigenic polymorphism, so that the mother is normally immunized by the alloantigen of paternal origin present in the syncytiotrophoblast. It is our belief that IgG antibody is required for continuation of the pregnancy, and that without this antibody, NK attack on the embryo results in miscarriage. The IgG antibody reacts only with the protein of the husband and about one in eight other men. This theory is nicely supported by Coulam et al. Am. J. Reprod. Immunol., 34: 333–337 (1995), who published a controlled study on the use of pooled normal human IgG as a means of passive immunization for the prevention of recurrent abortion in women. This form of passive immunization is accomplished. by transferring antibodies of a similar kind from female blood donors who have made antibodies to their partners' R80K allotypes. These anti-R80K antibodies cross-react with the patient's partner's antigens in the trophoblast. This is why up until the present invention, a woman was always immunized with her partners' cells.

We have discovered and do claim herein a novel monoclonal antibody which recognises an epitope on the R80K protein region of K562 cells and syncytiotrophoblasts and prevents the killing of these target cells. The monoclonal antibody is highly advantageous in that it reacts with a conserved site on the R80K protein on the surface of trophoblast cells in ALL human placentae. Therefore, the monoclonal antibody can be injected successfully into any pregnant woman and hence the woman would not require immunization with her partner's cells. As a result of the novel nature of this protective antibody, pregnant women would not be required to attend special care centres for treatment with their husbands cells and thus it could be less costly than current immunization and it could be available for safe use anywhere in the world.

It is therefore a further aspect of this invention to provide a means for initiating passive protection against NK induced abortion in women. The means for passive immunization would be in the form of a vaccine. The vaccine would include an effective dosage of the monoclonal antibody, BA11. It is a further embodiment that an antibody which is either an endogenous IgG antibody eluted from placentae or an IgG or IgM class monoclonal antibody may be used as a means for providing passive protection in women suffering from recurrent abortion. A monoclonal antibody towards a conserved epitope on the R80K antigen is preferred. Most preferably, a monoclonal antibody would be engineered to be of human IgG origin, inclusive of variable region specificity. The IgG antibody would be administered either parenterally, for example subcutaneously, intraperitoneally, intramuscularly or preferably, intravenously and would contain such preservatives as would be common in the manufacture of an immunoglobulin preparation. The great advantage of this new monoclonal antibody is that it could be used in anyone and could be injected successfully into any woman, thus not requiring immunization with her partner's cells. It is very fortunate that the BA11 monoclonal antibody also reacts with a similar protein in mice. This has allowed testing of the efficacy of the BA11 antibody to be studied in mouse models of miscarriage. BA11 inhibited abortion in three mouse. models, suppressing NK cytotoxicity of murine trophoblasts. These models are: the CBA×DBA/2 model with a high resorption rate of F1 embryos compared with parental strains, an endotoxin induced abortion/resorption model and a third model in which the pregnant mice were subjected to severe sonic stress. The BA11 antibody inhibited abortion in all three mouse abortion models. This reinforces that interference with NK killing can influence abortion/resorption in mice, and the BA11 antibody may effect similar results in analogous human situations (Example 4).

It should also be appreciated the BA11 monoclonal antibody (which would include the heavy and light chain of the BA11 antibody) as well as the binding site of the monoclonal antibody to the target cell which includes either the entire binding site or a portion of the binding site which would still be capable of active antibody binding (and thus protection of the target from NK killing) are all encompassed by this invention as well as a hybridoma which produces such a monoclonal antibody.

Use of a pure antibody, rather than use of a pooled source of normal human IgG is contemplated by this invention. It should be appreciated that due to this high degree of purity, dosage amounts typically administered under so-called "High Dose I.V. IgG" will not be required. Therefore, lower dosage amounts are contemplated under this method of passive immunization. Dosage amounts may be optimised by those skilled in the art taking into account patient weight, age and overall medical condition. Preparing such a dosage regimen will be well-known by those skilled in the art. A series of doses may be given for optimum inhibition of natural killer cell activity.

The BA11 monoclonal antibody is a preferred means for providing passive immunization in women suffering from recurrent abortion, since it has the advantage of being raised against a conserved epitope on the R80K antigen and hence works in all cases and not just those where a cross-reacting antibody is present. It is yet another aspect of this invention to provide an antibody directed to a monomorphic site on the placenta. Preferably this antibody will be of immunoglobulin class G, however class IgM antibodies are also intended for use in this invention. One of the main advantages provided by use of a monoclonal antibody is that the monoclonal antibody is directed towards a monomorphic site and thus can be used for treatment of women with problems of reoccurring abortion.

Diagnostic screening during early pregnancy using the BA11 monoclonal antibody is also envisaged by this invention. For instance, an ELISA assay system using the BA11 monoclonal antibody to capture the IgG and thus show levels of antibody present is one possibility. This would potentially indicate whether a woman would be at risk of miscarriage due to inappropriate antibody protection.

We conclude R80K is intimately involved in NK killing of target cells, and that a) a polymorphic alloantigenic site, and b) a monomorphic xenogenic site both can be used to inhibit NK killing during pregnancy by protecting with IgG antibodies to them.

Preferred features of each aspect of the invention are as for each other aspect, mutatis mutandis.

The invention will now be illustrated by the following examples. The examples refer to the accompanying drawings, in which:

Results are the mean of triplicate tests. Two eluted IgG preparations which showed complement dependent cytotoxicity to K562 were chosen and two that did not. Both the reactive eluates, p343 and p336, showed 50% inhibition of NK killing at about 70 ng per tube. The human serum, pooled normal human IgG and the eluates without specifying for K562, p384 and p390 did not inhibit NK killing.

Figure 15:
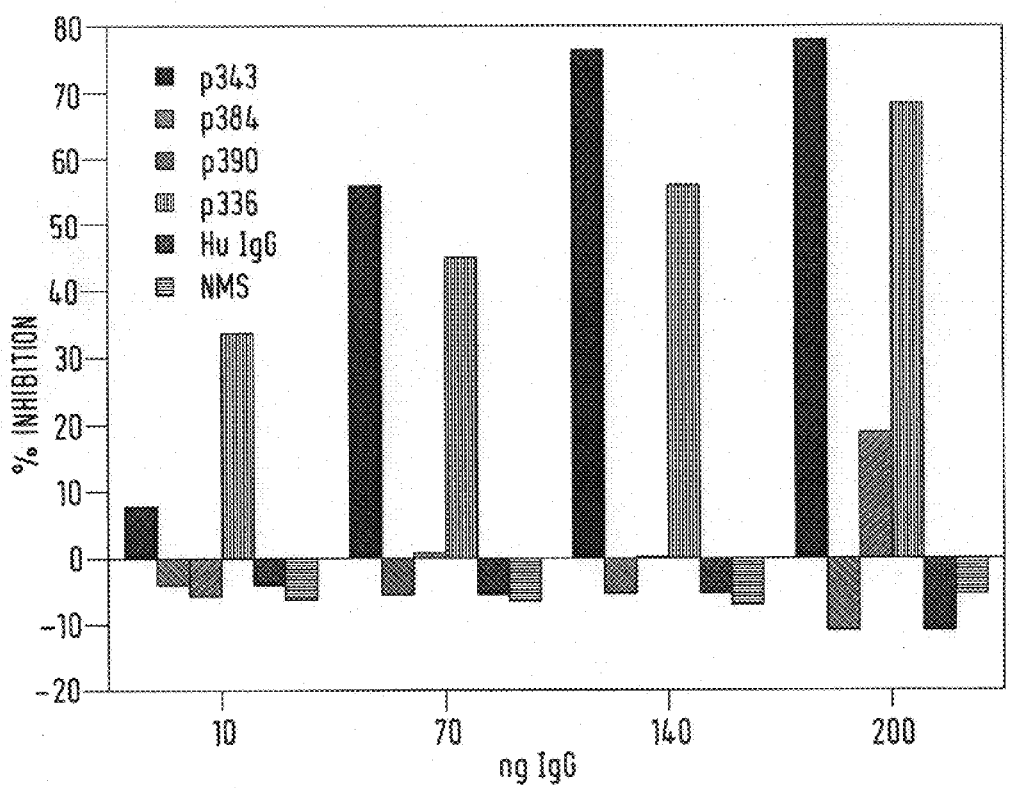
FIG. 15 represents studies of inhibition of NK killing of K562 with eluted antibodies from microvesicles, normal male serum and pooled human IgG preparations. $^{51}$Cr labelled K562 cells were incubated with human peripheral blood mononuclear cells for 3.5 hours. Results expressed as the percentage reduction in chromium release with the test sample compared with a culture without inhibitor.
Figure 16:
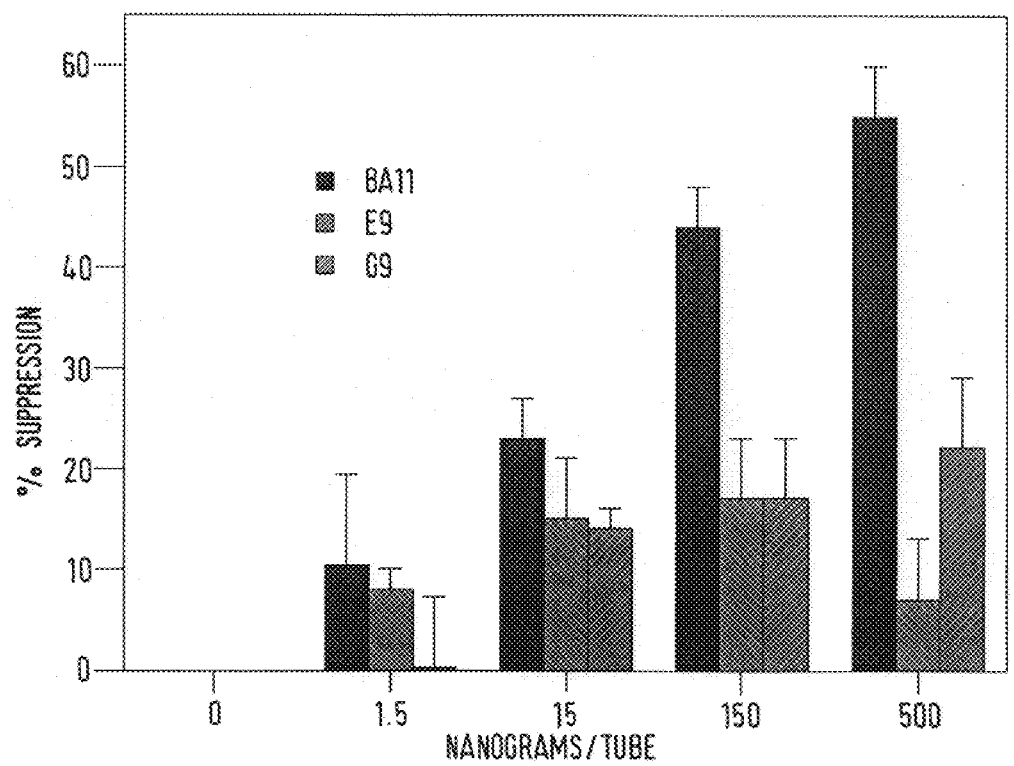

FIG. 16 shows inhibition by three hybridoma clones of $^{15}$Cr release from labelled K562 cells in the presence of human peripheral blood mononuclear cells. All three clones reacted with the R80K molecule by solid phase radioimmunoassay. As with the assay of eluted antibodies from microvesicles (FIG. 15), results are expressed as the mean percent inhibition of triplicate cultures. Of the three clones, only BA11 showed dose dependent inhibition of Nk cytotoxicity. The immunoglobulin concentration required to produce 50% inhibition was comparable with that found for eluted IgG in FIG. 15.

FIG. 17 details the reactions of $AB_e$ with acidified and unacidified microvesicle preparations. The antibody only reacts with the preparation after acid elution of the antibody. When the $Ab_e$ was absorbed with the tryptic fragment of R80K, its binding to $V_a$ was abolished. IgG binding detected with $^{125}$I-Protein A.

FIG. 18 shows the reaction of $V_a$ from 12 horse placentae with the 12 eluted antibodies ($Ab_e$) from the same placentae. Results are expressed as (counts bound in sample)/(counts bound with isologous $V_a$). It will be seen that there is strong reaction with their own acidified vesicles, but only 18/132 (13.6%) reactions are seen with those of another placenta. The upper limit of nonspecific binding of normal male horse IgG was 0.6 of the isologous value, and reactions above this level were considered positive.

FIG. 19 shows complement dependent cytotoxicity of 14 $Ab_e$ out of a total of 28 which reacted with at leat one of four human lymphoblastoid cell lines. Cytotoxicity is shown as percentage kill, duplicate estimations are indicated for each test, unscorable wells are indicated as ns. Significant results are boldened, and represent a mean value more than 20% above the background kill for that antibody. 24/112 tests (21%) were positive.

EXAMPLES

Example 1

Alloantibody

Figure 1:
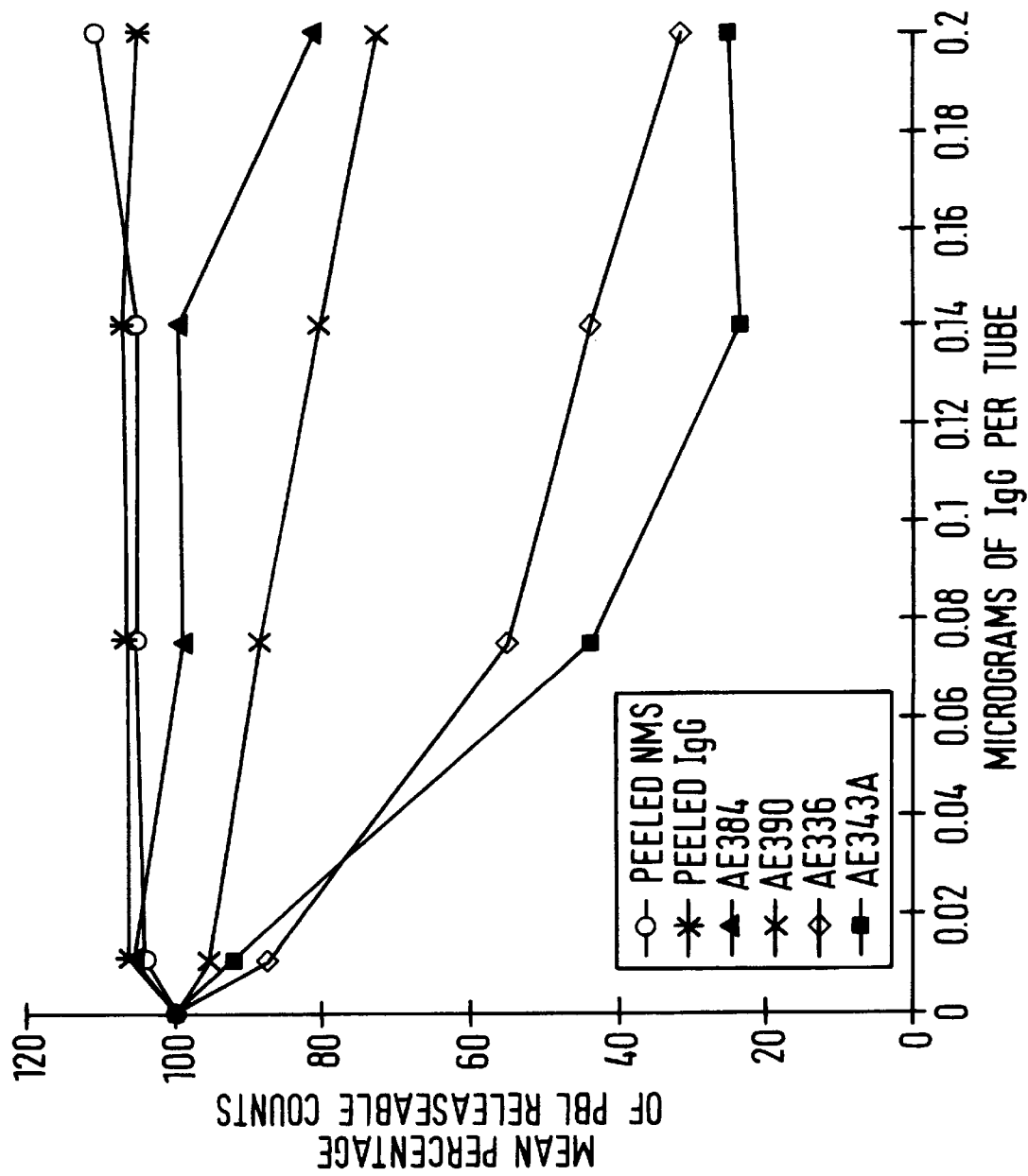
FIG. 1 shows the inhibition of NK killing of K562 produced by eluted antibodies from placentae. AE336 and AE363A bound to K562 and inhibited NK killing >50% at 0.07 $\mu$g. The others which did not bind to K562 did not inhibit killing.

Eluates of IgG antibody from 74 term human placentae were made, using pH 3 citrate buffer. The eluates were standardised to have the same concentration of IgG, and then tested against K562 cells cultured in RPMI 1640 containing 10% fetal calf serum, using complement dependent cytotoxicity in an NIH long cross match technique. Eluates with specificity for the K562 cells were considered as those percent killing of more than 20% above background kills in duplicate estimations. Table I schematically represents these two eluates, and the high cytotoxicity of K562 in the presence of complement derived from rabbit serum. These antibodies, and several that were negative were tested with pooled normal human IgG, and normal human sera for inhibition of NK killing of K562. To polystyrene tubes containing 50,000 K562 cells was added dilutions of the eluates, and they were incubated at 37° C. for 30 minutes. Approximately 250,000 human peripheral blood lymphocytes obtained by sedimentation of citrated human blood in Lymphprep were added and incubation of the mixture continued for an additional 4 hours. FIG. 1 shows that the two eluates with specificity for K562 both inhibited NK killing at concentrations of about 100 ng/ml, and that all other preparations of IgG did not inhibit killing until much higher concentrations were used.

A similar study of the two eluates was made with LAK cells, made by 48 hours incubation of PEL with IL-2. After the incubation the cells were used as source of LAK cells and the experiment described above repeated. Similar inhibition of killing was obtained with these antibodies, although the killing obtained in the absence of inhibitor was greater than obtained with the NK preparations.

Example 2

Monoclonal Antibodies

Figure 2:
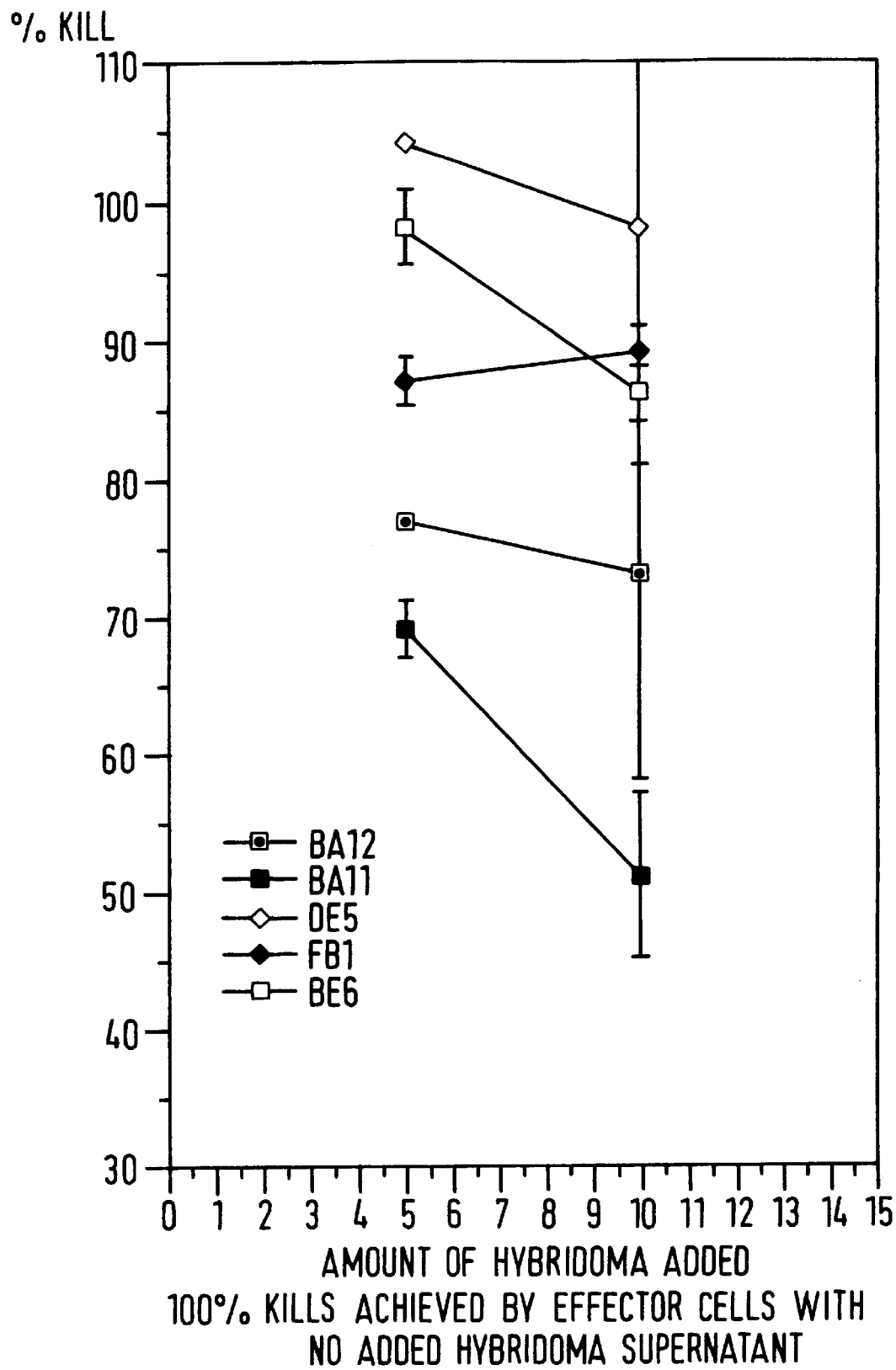
FIG. 2 shows the inhibition of NK killing of K562 by hybridoma supernatants. BA11 and BE6 show significant inhibition but the others do not. All monoclonals have affinity for microvesicle proteins.
Figure 3:
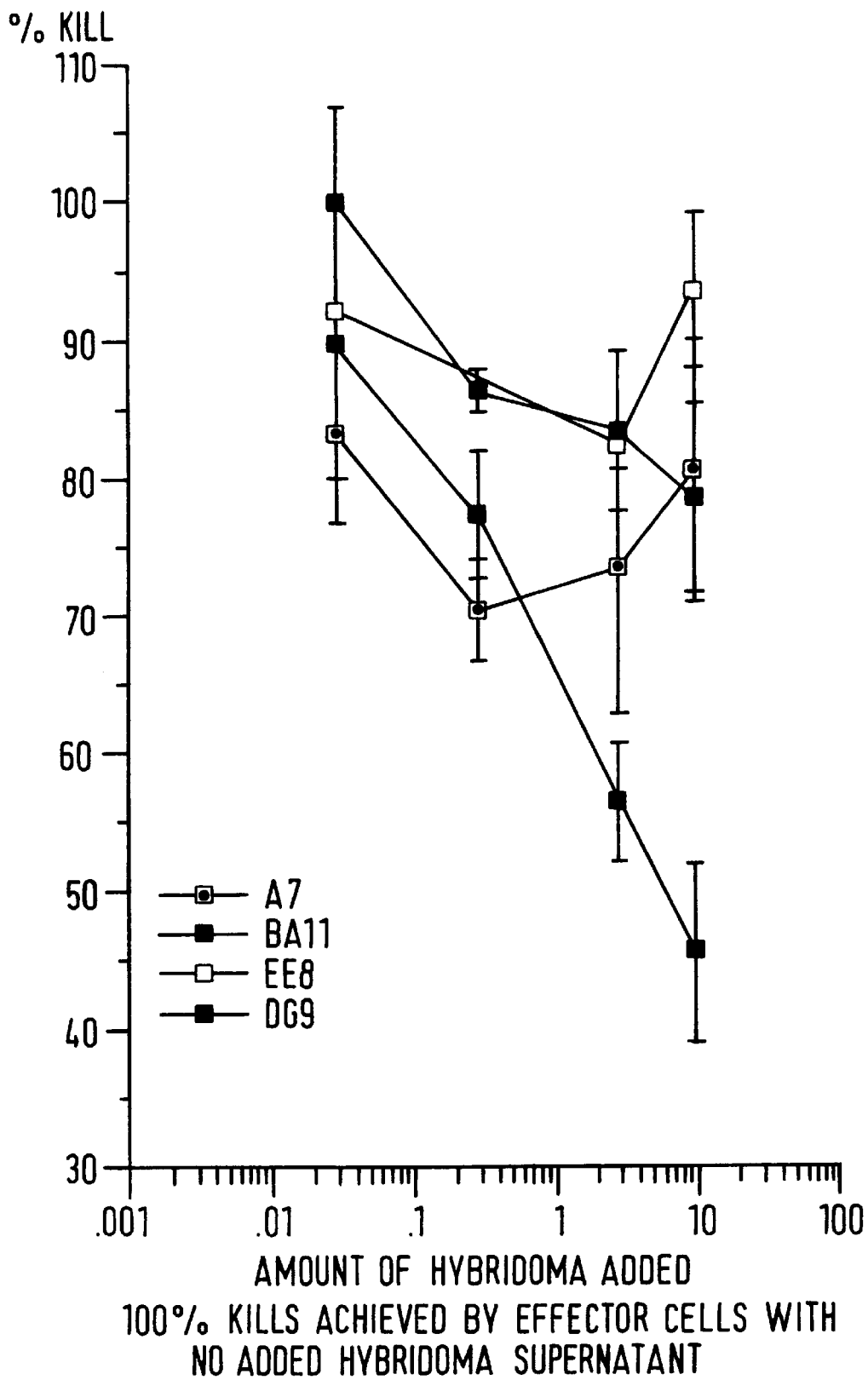
FIG. 3 shows four monoclonals reacting with R80K. Only BA11 shows inhibition of NK killing of K562, which is below 50% at 4 microlitres (75 nanograms).

Hybridomas were prepared from mice immunized with microvesicles of human placenta which had been treated with citrate buffer pH 3 to remove the IgG antibody. The clones which bound to syncytiotrophoblast microvesicles were detected using a dot blot assay on nitrocellulose membranes, with detergent solubilized acidified vesicles adsorbed to the membrane, the hybridoma culture supernatants added, and binding detected with an enzyme labelled anti-mouse IgG antibody. The 50 clones obtained were tested for binding to R80K using a sandwich capture assay. Tubes were coated with IgG eluted for vesicles of one placenta, and the antibody was used to capture the detergent-solubilized acid treated vesicle proteins. The hybridoma supernatants were then added to the tubes, and binding of the Mab to the antigen revealed using enzyme labelled anti-mouse IgG antibody. Table IV shows that three clones reacting with R80K were obtained, BA11, DG9 and EE8. These were tested for the ability to inhibit NK killing as described above. FIGS. 2 and 3 show that there was strong inhibition of killing by BA11, but the other two did not inhibit measurably at the same concentrations.

In order to demonstrate that the epitopes detected by the Mabs were different, the capture assay described using alloantibody to capture the antigen was repeated, using each Mab as the capture antibody in turn. BA11 binding to R80K did not affect the binding of BG9 or EE8. As the initial sandwich assay was carried out using the alloantibody, it appears that the alloantigenic epitope and the epitope binding BA11 are separate. In addition, the BA11 epitope is different from that of the other two Mabs. Table V shows that BA11 binds to R80K obtained from several different placentae, unlike the IgG antibodies obtained by acid dissociation, which only bound to the homologous R80K. Thus although the alloantigenic epitope is highly polymorphic the BA11 site is monomorphic, although both antibodies can inhibit NK/LAK activity of K562.

T and B Lymphocytes

Lymphocytes were prepared by density gradient centrifugation of citrated blood samples on Lymphoprep (Nycomed, Oslo, Norway). The cells were washed and resuspended in Hank's solution at a concentration of $10^6$ cells/ml. B lymphocytes were separated using AET-treated sheep red cells (Pellegrino et al., *Clin. Immunol. Path.* 3 324–333 (1975)). The unrosetted B lymphocytes were washed and resuspended in Hank's solution (BSS). The rosettes were treated with 1 ml of fresh human serum diluted with an equal volume of BSS to lyse the sheep red cells. The T lymphocytes were washed and resuspended in BSS. Cytotoxic antibody testing was carried out by the long NIH method (Mittel et al., *Transplantation* 6 913–927 (1968)), using rabbit serum as complement source (Buxted Rabbit Farms, East Grinstead, UK). All wells with a kill 10% above that of the control wells containing normal human serum were recorded as positive. When testing sera for antibodies specific to B lymphocytes antigens the incubation period was twice as long as that described for T lymphocytes.

Dextran Cells

One ml of 6% dextran in saline was added to 10 ml of citrated human or horse blood. The cells were allowed to sediment for 30 min at room temperature. The supernatant cells were washed and resuspended in phosphate buffered saline (PBS). When pure monocytes were required, the dextran cells were layered over Nycoprep (Nycomed, Oslo, Norway), and after centrifugation the banded cells were harvested, washed and resuspended in PBS.

Preparation of Microvilli

Using the method of Smith, Brush and Luckett (*Nature* 252 302–303 (1974)), microvilli were prepared from fresh term placentae. Fresh placentae were washed in cold barbitone buffered saline containing 10 mM $CaCl_2$ and 5 mM $MgCl_2$ and any adhering clots and membranes removed. The chorionic villi were originally disrupted from the underlying tissue by scraping with a plastic ruler; this technique was modified, and the cleaned, whole placenta placed in cold PBS in a beaker, and then gently agitated with a vibrating mixer (Vibromixer, Chemap AG, Bonn, Germany) for 30 min at 4° C. This method caused much less disruption of cells, and gave a much purer preparation of microvilli. The resulting suspension was centrifuged at 500 g in a MSE 4L centrifuge for 20 min at 4° C. and the microvesicle containing supernatant carefully removed, and centrifuged in an International B20 centrifuge at 4° C. for 60 minutes at 11,000 g. The pellet of microvesicles was resuspended in 20 ml PBS, and centrifuged at 500 g for 20 min in a bench centrifuge to remove aggregated material. The supernatant was aliquotted in 2 ml portions and stored at −70° C. until required.

Acid Elution of IgG from Microvesicles 2 ml microvesicle suspension was centrifuged at 24,000 g for 10 min at 4° C. in an Eppendorf microcentrifuged (Eppendorf AG, Hamburg, Germany). The sedimented vesicles were suspended in 0.05M citrate pH 3.0 and left at room temperature for 60 min. The acid treated vesicles ($V_a$) were removed by centrifugation and resuspended in PBS. The supernatant which contains the acid eluted antibody ($A_e$) was dialyzed against PBS at 4° C. overnight, and stored at −70° C. The IgG concentration was determined single radial immunodiffusion using a rabbit antihuman IgG antibody.

Binding of $A_e$ to Peripheral Blood Cells

To detect antibodies to lymphocyte surface antigen, a panel of male lymphocytes were used in the long NIH cross match (Pellegrino et al., *Clin. Immunol. Path.* 3 324–333

(1975)), using $Ab_e$ from different placentae. Human and horse peripheral blood lymphocytes and dextran prepared mononuclear cells were exposed to $Ab_e$ of both human and horse placentae. Binding of the eluted antibody to the cells was measured by exposing the human cells to $^{125}$I-labelled Protein A, and the horse cells to $^{125}$I-Protein G, after they had been incubated with $Ab_e$.

FACS analysis was carried out on cells stained with fluorescein-labelled antibodies (Hayakima et al., *J. Exp. Med.* 157 202 (1983)). After staining the cell pellet was resuspended in 100 μl of 1% formaldehyde in PBS and studied in a FACS 4 analyser with a FACS LITE laser (Becton Dickson, Oxford, UK).

SDS-PAGE Electrophoresis

Electrophoresis was carried out in a BioRad vertical chamber (Bio-Rad Labs Ltd, Hertford) in 10% acrylamide gels. Electrophoresis for 4 hrs was followed by blotting onto nitrocellulose paper (Schleicher & Schuell BA 85, Anderman & Co, Kingston, UK). Proteins were stained with BioRad colloidal silver stain or amido black 10B. The western blots were prepared by applying the antibody to the membrane preblocked with Marvel (Cadbury, Stafford, UK), heat-sealed in nylon bags. After staining, the bags were opened, the membranes washed, developing antibody added and the membranes resealed in fresh bags for 48 hours to allow reconfiguration. They were then washed and the enzyme stain revealed with a diaminobenzidine/$H_2O_2$ mixture.

Trypsin Digestion of Microvesicles

Both untreated and acid treated microvesicles were digested with 1 mg/ml trypsin for 15 min in 0.15M tris/HCl pH 8.1. The release of antigen was studied by coating 2.5 ml polystyrene tubes with the supernatant of the digestion, and then applying the $Ab_e$ of the same placenta. The binding of $Ab_e$ was studied by measurement of the adherence of $^{125}$I-labelled Protein A to the tubes.

Although proteins other than IgG are eluted, it may be that the bound IgG antibody protects the R80K protein from tryptic digestion. When $V_a$ were used however, an antigenic fragment reacting with the $Ab_e$ was released. SDS-PAGE analysis of the released material showed several protein bands. After blotting onto nitrocellulose membrane, eluted antibody was applied, and the blot stained with peroxidase-labelled protein A.

Horse Placental Microvesicles

Horse microvesicles were prepared from placentae in a similar manner to the human ones, differing only in that a 25×25 cm piece of the flat sheet of placenta was used (the horse placenta is a large flat membrane covered with trophoblast, with a microvesicular surface on its maternal aspect). The sheet of placenta was stapled to a PVC board, and placed in a rocking chamber, with 400 ml of fluid. 60–90 reciprocations/min produced a smooth wave which swept across the maternal surface of the placenta. This produced clean microvesicles with a good yield.

Acid Dissociation and Reassociation of IgG and Microvesicle Antigen

Figure 7:
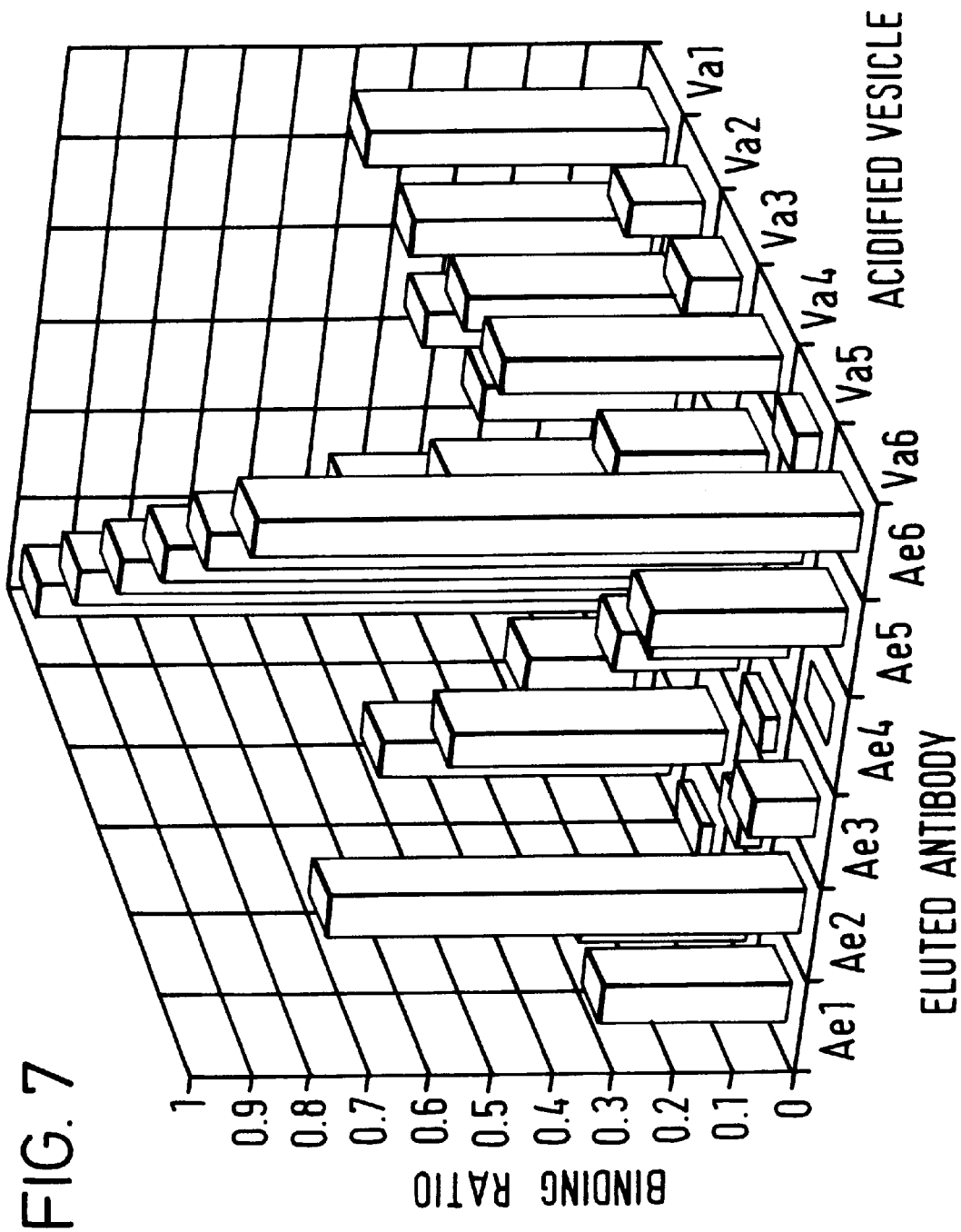
FIG. 7 details the reaction of six $^{125}$I-labelled $AB_e$ with the $V_a$ from which they were eluted. Values shown are the fraction of the binding of IgG present when the eluate was applied to the isologous vesicle preparation, i.e. from the same placenta. The mean non-specific binding of normal male human IgG was 0.25. 5/30 (16.7%) samples were above the upper confidence limit of 0.47.

All the microvesicles from more than 700 placentae were found to have IgG bound to an epitope on the trophoblast antigen. There was a wide variation in the amount of IgG eluted from the placentae initially reported (Jalali et al., *Transplant Proc.* 81 572–574 (1989)), but with a more standardised method of preparation this is less. The IgG eluted at pH 3 binds back to the neutralised microvesicles, but not to untreated vesicles from the same or other placentae (Table I). This implies that the antigen is covered with antibody in all the term placentae studied. The neutralised antibody readily binds back to the $V_a$ from which it was dissociated and will bind to $V_a$ preparations from 16.7% of other placentae, implying considerable antigenic polymorphism (FIG. 7).

A similar polymorphism was found with eluted antibodies from horse placentae, where 13.6% of unrelated placentae showed significant binding of the eluted IgG, using $^{125}$I-labelled Protein G on the $Ab_e$ for its detection (Table II).

Binding of $A_e$ to Peripheral Blood Cells

Figure 8:
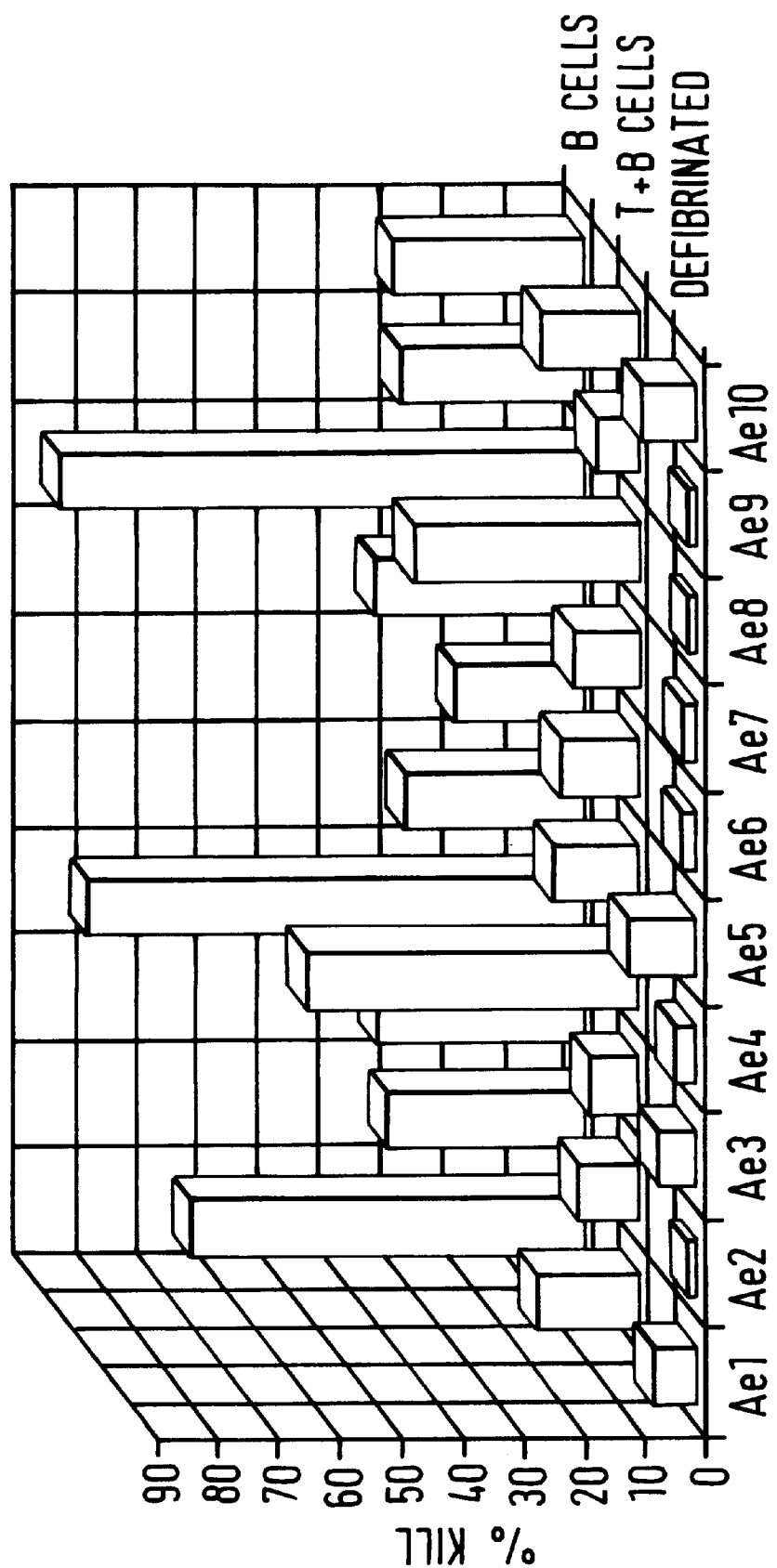
FIG. 8 shows the reaction of ten $AB_e$ with PBL of a normal male donor. Three cell fractions were tested, T+B (Lymphoprep cells), B lymphocytes, and B depleted T lymphocytes (Lymphoprep cells from defibrinated blood). Higher percentage kills were shown with B than with T+B lymphocytes, and the B depleted cells did not shown reactions.
Figure 9:
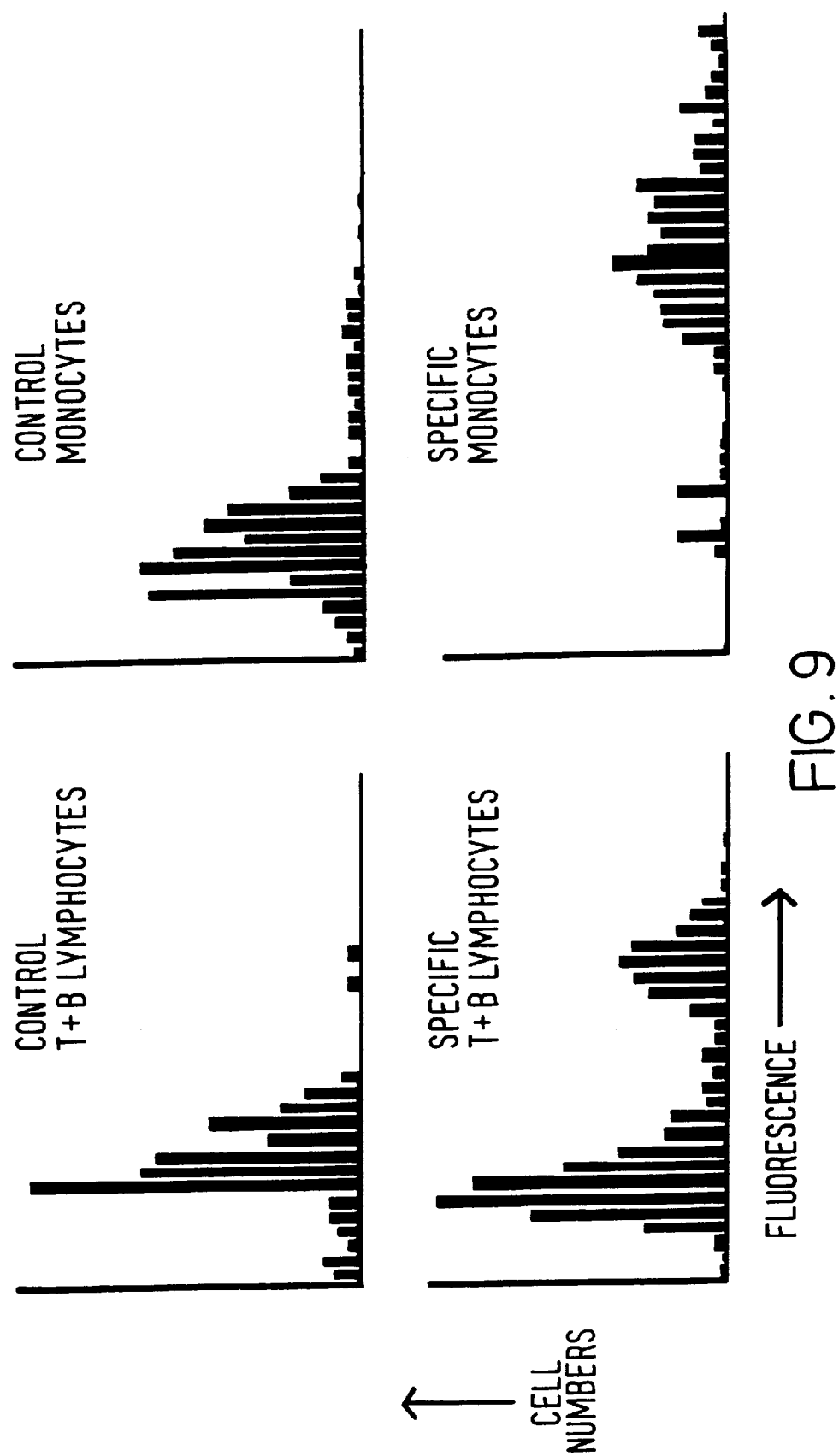
FIG. 9 shows the FACS analysis of human dextran PBL fractions stained with two $AB_e$ preparations, one reacting specifically and one control. T+B lymphocytes were made with Lymphoprep, and monocytes with Nycoprep. FITC-labelled anti-human IgG was used to identify bound antibody. Only the B lymphocytes in the Lymphoprep cells show binding of the positive antibody, but virtually all the monocytes in the Nycoprep preparation are stained.
Figure 10:
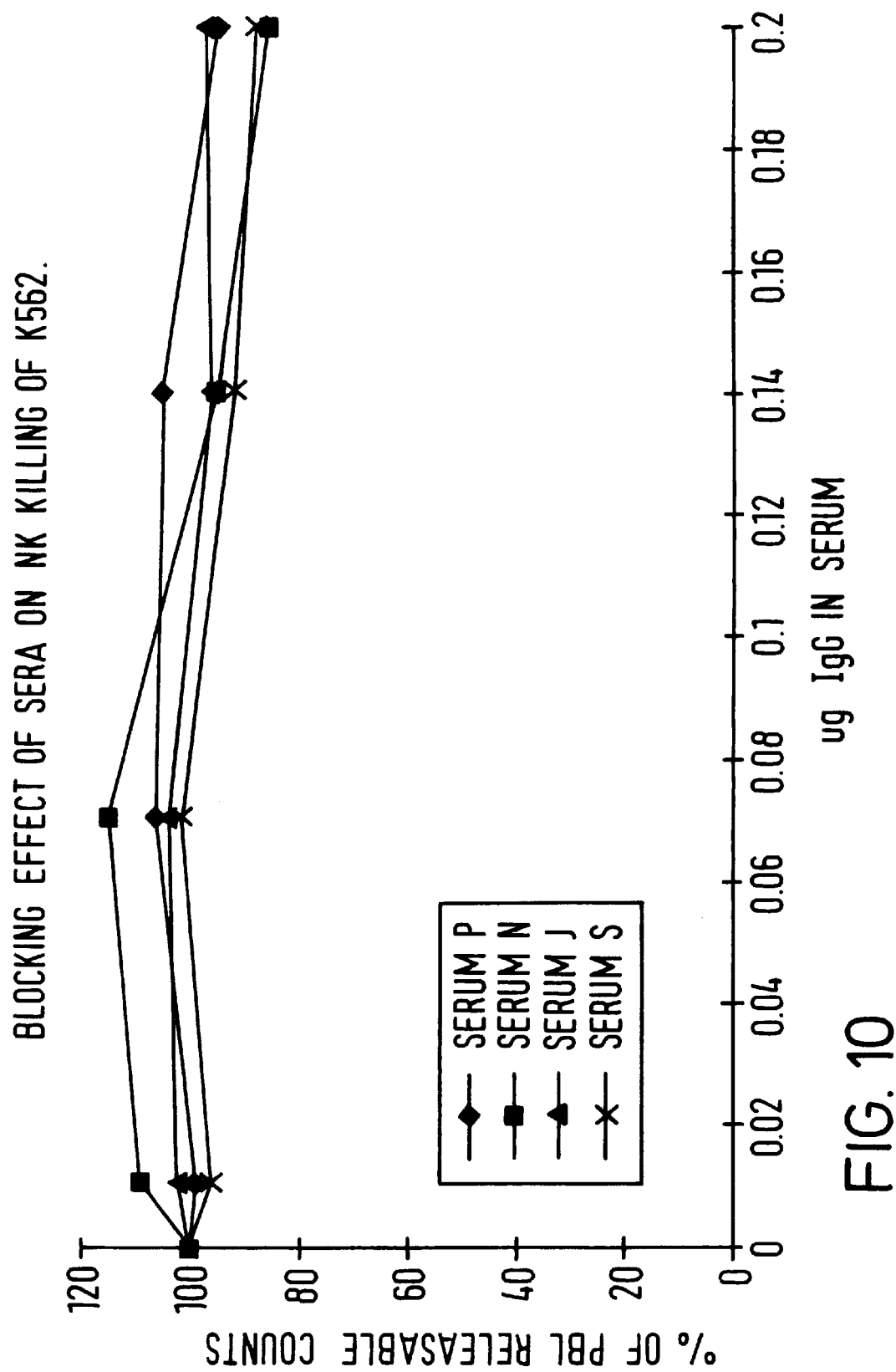
FIG. 10 shows normal human sera without anti-K562 antibodies do not inhibit NK killing of K562 cells, even at 200 micrograms.
Figure 11:
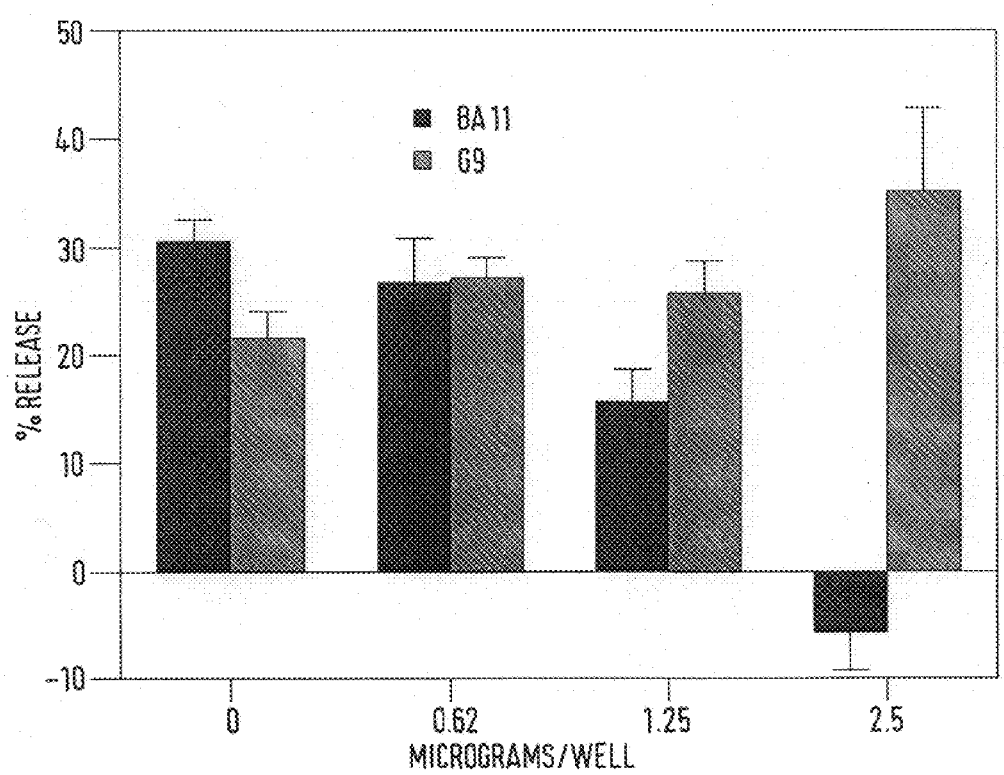
FIG. 11 demonstrates graphically the effect of addition of BA11 or G9 to cultures of murine trophoblast cells and murine spleen cells as a source of NK cells. results are released of label as percentage of the maximum released by detergent less the background release. By Student's t test the reductions in toxicity with BA11 compared with G9 at 3.13 ug and 6.25 ug are significant (p=0.015 for 3.13 ug/well and p=0.005 at 6.25 ug).
Figure 12:
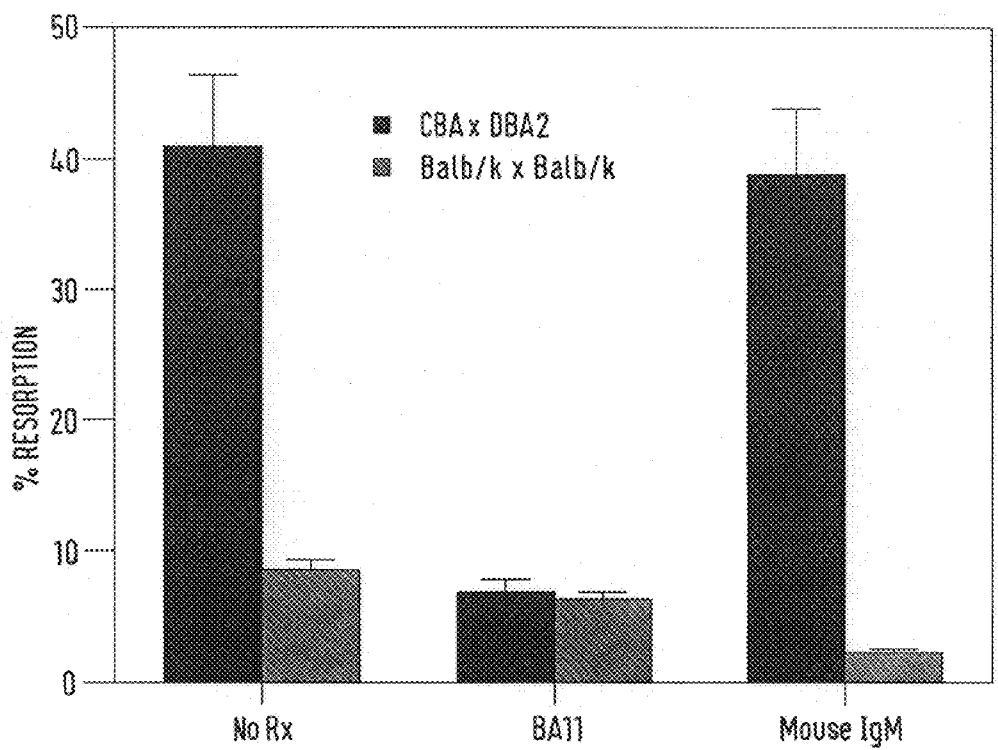
FIG. 12 demonstrates graphically the effect of injection of BA11 or normal mouse IgM on resorption rates in CEA×DBA2 matings and Balb/k×Balb/k. Each pregnant mouse was given 250 ng of BA11 or control intraperitoneally on days 6, 8 and 10 of pregnancy. Error bars indicate + or − one SD. Without treatment resorption occurred in 16/39 implants (41%). With BA11 3/43 implants resorbed and with the control injection 14/36 implantations resorbed. Injection BA11 was significantly different from no injection or control injection by $X^2$ analysis (p<$10^{-6}$).
Figure 13:
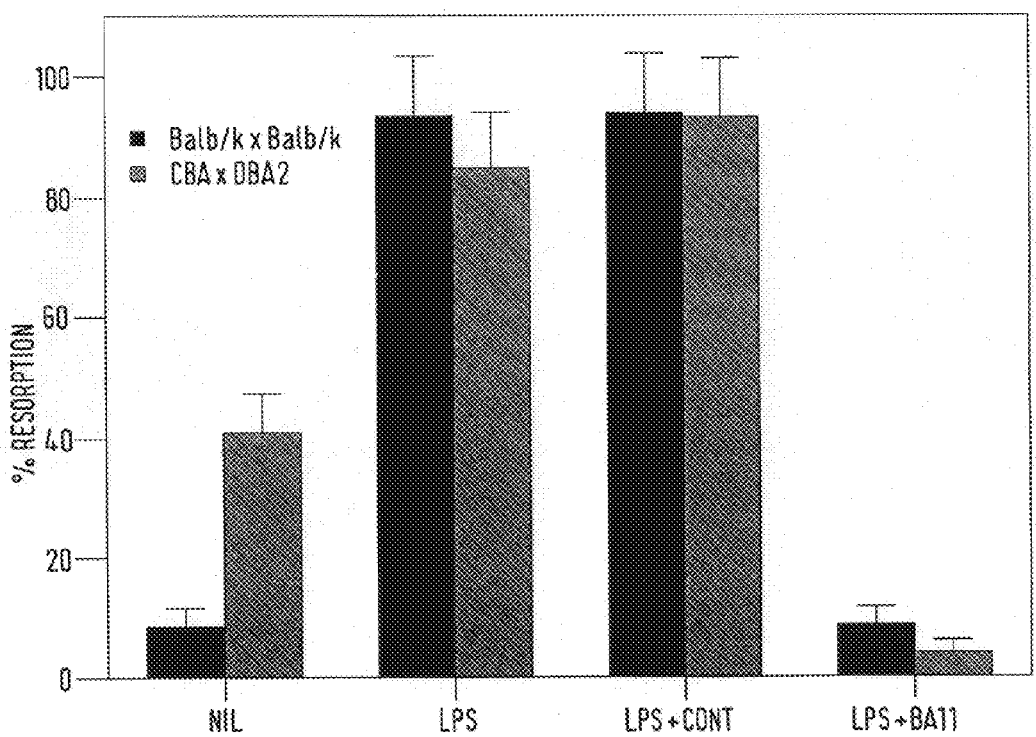
FIG. 13 demonstrates graphically the effect of 10 ug injections of BA11 or control mouse IgM on days 4.5, 5.5 and 6.5 on the resorption of implants in CBA×DBA/2 and Balb/k×Balb/k matings. A high rate of resorption was induced by injection of LPS on days 6.5, 8.5, and 10.5. Treatment with BA11 resulted in a resorption rate less than 5% for both strain combinations compared with rates of more than 80% for untreated or control injection groups. The difference for both groups is significant by $X^2$ analysis (p<$10^{-6}$ for both CBA×DBA/2 and Balb/k×Balb/k).

FIG. 8 shows that when cytotoxicity of T+B lymphocyte cells from one human male donor by 10 $A_e$ were tested there were reactions in two wells, but the highest kill was only about 50%. Higher kills were observed with the purified B lymphocyte preparation from the same donor, but no significant killing was observed when B depleted cells were tested (from defibrinated blood). Preparations of dextran cells were then fractionated on Lymphoprep to produce T+B lymphocytes with some monocytes, and Nycoprep was used to produce a pure monocyte preparation. FACS analysis shows that the Lymphoprep preparation has some cells reacting with the $Ab_e$ which reacted with the dextran cells, and virtually all the Nycoprep cells reacted with the antibody (FIG. 9). Quantitative binding studies with these cell fractions showed that the binding of the B lymphocytes in the lymphoprep fraction and the monocytes in the Nycoprep fraction accounted for all of the total binding found with starting dextran cells.

Similar results have been obtained with horse peripheral blood cells, using horse $A_e$ reacted with the blood cells and binding measured by exposure to $^{125}$I-labelled protein G (Table II). No cross species binding was detected.

Reactivity with HLA Homozygous EBV Lymphoblastoid B Cell Lines

A panel of $A_e$ from different human placentae were tested for cytotoxic activity against four different EBV transformed lymphoblastoid cell lines, all of which were homozygous for the HLA A1-B8-Dr3 haplotype. The mean value of the duplicate estimations was considered positive if it was more than 20% above the background control kill with normal male human serum. If the trophoblast antigen were MHC related, identical reactions would be expected for each cell line. From Table III it can be seen that there is, in contrast, a pattern of different reactivity for different cell lines, making an M-MHC association very improbable.

Purification of the 80 kDa Antigen Molecule

Figure 4:
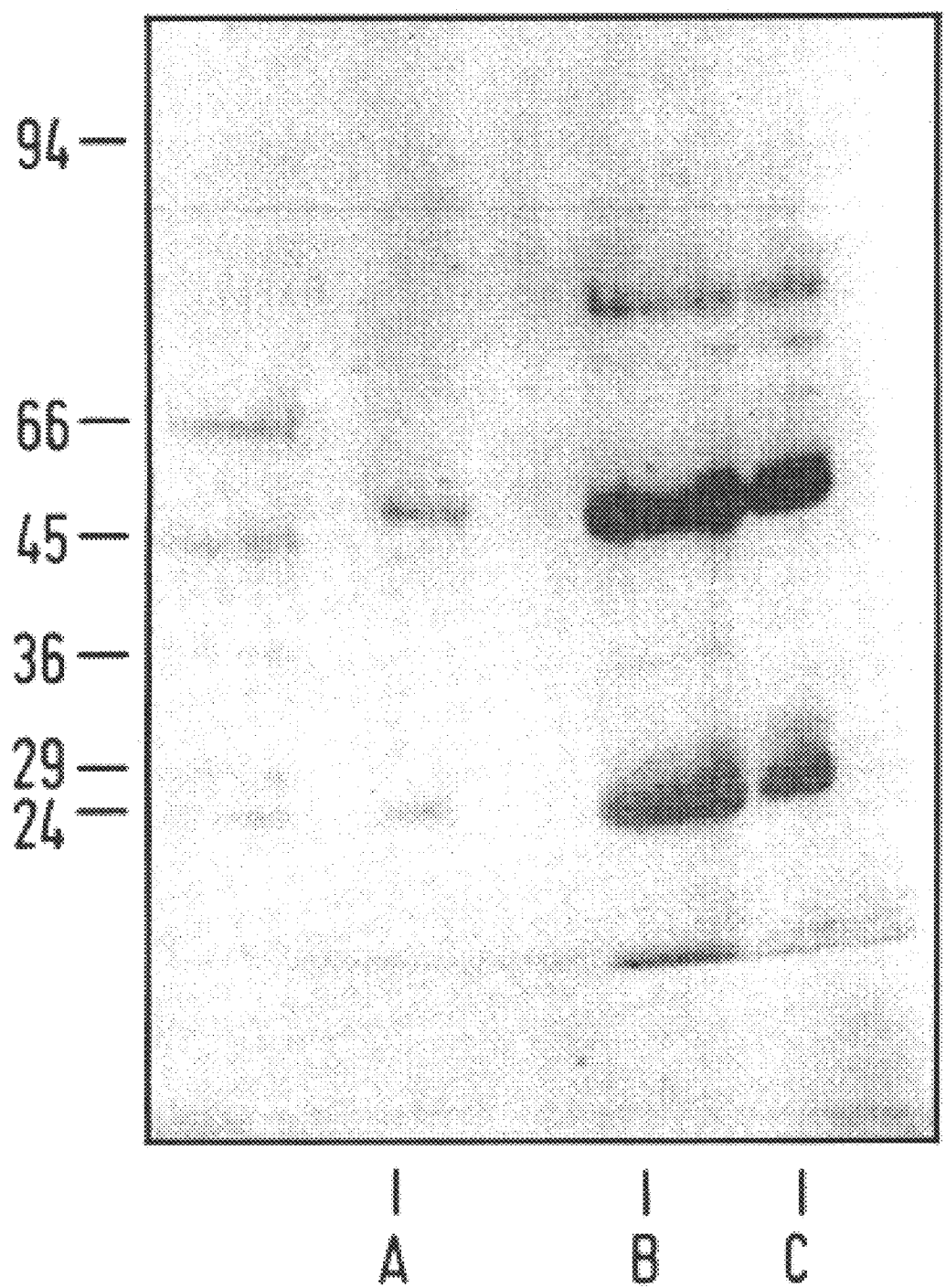
FIG. 4 shows SDS-PAGE electrophoresis of deoxycholate solubilised $V_a$ proteins affinity purified by chromatography on Protein A-Sepharose. Heavy and light chain bands of IgG, and a prominent 80 kDa band are visible. The fainter band at 72 kDa represents an impurity, not present in most preparations of the affinity purified antigen. Track A is human IgG. Tracks B and C are two preparations from different placentae.

The deoxycholate-solubilized crude microvesicle preparation from all of one placenta was applied to a Protein A-Sepharose affinity FPLC column and eluted with 0.2 M pH 3 sodium citrate. The eluted fraction was subjected to SDS-PAGE electrophoresis in 10% gels. Heavy and light chains of IgG and an 80 kDa band are shown (FIG. 4). This band is evident in all the experiments with a number of different placental preparations, the measured size varying from 76–82 kDa in different preparations, but when several samples from different placentae were electrophoresed in adjacent wells there was no evidence of size heterogeneity. The protein has thus been designated R80K.

Example 3

Trypsin Digestion of Microvesicle Antigen Releases a 50 kDa Fragment

Figure 5:
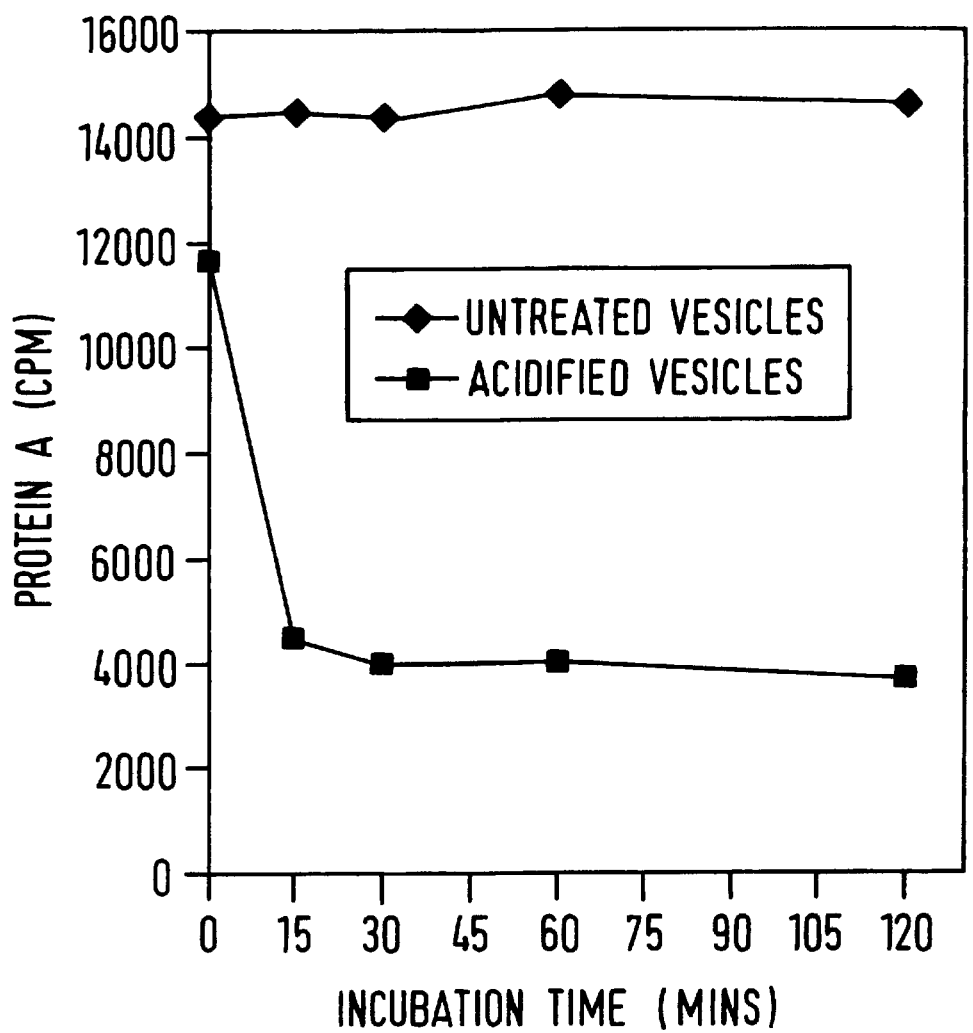
FIG. 5 shows trypsin digestion of microvesicles. There was no release of IgG from untreated vesicles incubated with trypsin, as shown by the binding of $^{125}$I-Protein A with acid treated vesicles tested by incubating with the antibody eluted from them, Protein A binding was virtually abolished after 15 mins incubation with trypsin, showing loss of the surface R80K antigen. It appears that R80K covered with IgG antibody is resistant to cleavage by trypsin.

Trypsin digestion of the microvesicles did not release an antigenic fragment. When acid treated vesicles were treated with trypsin a fragment reacting specifically with the eluted antibody was released (FIG. 5).

Figure 6:
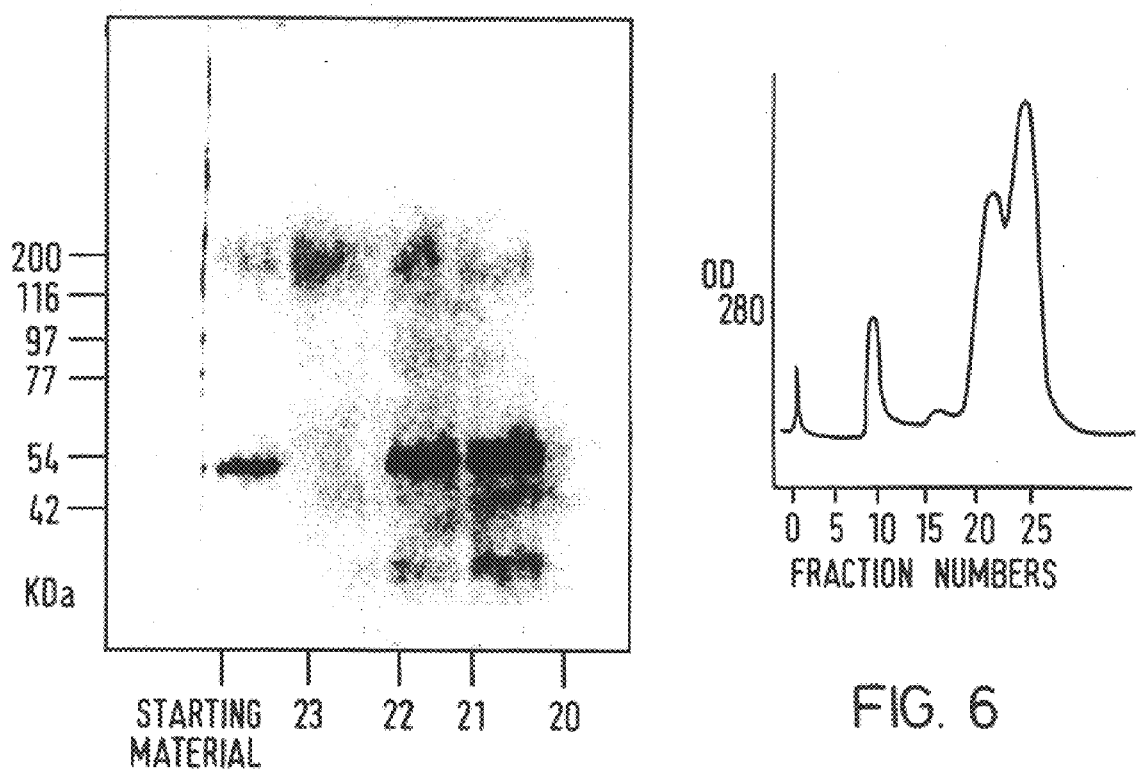
FIG. 6 shows Western blot of the fractions obtained by gel filtration of the trypsin digest of acidified microvesicles. The blots were exposed to the acid-eluted antibody from the vesicles, and then to peroxidase labelled anti-human IgG. The track numbers correspond to the column fraction numbers showing the chromatogram tracing.

Although the deoxycholate-solubilised material from acidified microvesicles appeared as a band at 80 kDa, the trypsin eluted fragment stained by $Ab_e$ was at the 50 kDa position. This fragment did not show the aggregation, and tendency to bind to hydrophobic surfaces, of the detergent solubilised molecule and remained dispersed in solution in the absence of detergent. It was stable on freezing and thawing, and could be stored for long periods at −70° C. without loss of antigenicity. Fractionation by FPLC of the trypsin solubilised material resolved four protein peaks reacting with the appropriate $A_e$. The antigenic material reacting with the $Ab_e$ lay between the third and fourth peaks. Western blots of this area stained with isologous $Ab_e$ revealed a single 50 kDa protein (FIG. 6). The staining of a very low molecular weight band in the track with tube 21 is probably artefactual. The fragment was capable of absorbing out of the specific antibody, and preventing it binding to its target $V_a$ (Table I).

The antibody although raised in mice against human trophoblast, reacts with a presumably homologous murine antigen. Two attempts have been made to inhibit the NK cell mediated abortion models in mice.

In the first, carried out by G. Chaouat in Paris, there is a well known system of inducing quite high abortion/resorption rates in pregnant mice by producing F1 pregnancies in CBA×DBA2. About 40% of embryos die and are reabsorbed in untreated mice. The mechanism has been shown to be mediated through NK cells, and inhibited by removal of these cells, prevention of their activation, or by immunising the mothers with paternal strain cells. Two trials were conducted in which the mouse were given 200 microlitres of hybridoma culture supernatant injected intraperitoneally on days 4.5, 6.5 and 8.5 of pregnancy. The untreated mice (20) had a resorption rate of 28% of their embryos and the BA11 treated had 6% resorption. The difference is statistically significant ($0.05 < p < 0.02$). This latter figure is about the background abortion rate found in other strain combinations or inbred matings.

In the second set of experiments carried out for us in Hamilton Ontario by Dr. D. A. Clark, pregnant mice were subjected to sonic stress, using a recorded sound used to repel moles. This again produces a high resorption rate. The mice were treated with BA11 or the control DG9 antibody. The mouse treated with BA11 had an 8% resorption rate compared with 35% in the controls (20 mice per group). Mice not subjected to the sonic stress had a resorption rate of 11% with the DG9 and 4% with BA11. The difference in induced abortion in the BA11 and DG9 groups was statistically significant ($p < 0.5$).

These experiments indicate clearly that abortion due to NK killing of the embryos is prevented in two mouse models due to injection of the BA11 monoclonal antibody of this invention.

Example 4

Human NK Killing Assay

Monoclonal Antibodies: Mice are immunized with human term placental microvesicles which were treated with citrate buffer (pH 3.0) to remove the IgG antibody bound to the vesicles. Hybridomata are prepared from the mouse spleen cells after three immunizing doses, and cultures screened for antibody to the R80K protein antigen. A solid phase assay is used in which IgG (acid eluted from the microvesicle preparation) is applied to plates coated with protein A. Acid treated microvesicles solubilized in deoxycholate are then applied to bind the R80K protein to its IgG antibody. The hybridoma supernatants then are added and those which contain monoclonal antibodies with specificity for R80K will bind mouse immunoglobulin to the plates. Peroxidase labelled anti-murine immunoglobulin (DAKO Ltd, High Wycombe, Buckinghamshire, England) is then added and the enzyme detected with orthophenylene diamine and hydrogen peroxide. All applications and washings are in 0.05% Tween 20 in 0.01M EDTA, 0.15M sodium chloride (pH 7.4).

Assay

K562 human cell cultures are used as targets. Overnight subcultures of cells are radiolabelled with $^{51}Cr$ sodium chromate by incubation in RPMI 1640 for 60 minutes, washed twice with RPMI 1640 and resuspended at a concentration of $1 \times 10^6$ per ml. Human peripheral blood (PBMC) mononuclear cells are prepared from citrated normal human blood, by centrifugation over a gradient of Lymphoprep (Nygaard, Oslo, Norway). The mononuclear cells are suspended in RPMI 1640 at a final concentration of $5 \times 10^6$ per ml. In each culture $10^4$ labelled K562 cells and $5 \times 10^5$ PBMC are incubated in a total volume of 200 ul. After 3.5 hours, three tubes of each experimental group are centrifuged and the pellet and supernatant counted separately in a Packard Multi-Prias gamma counter. Results are expressed as the fraction of the counts released into the supernatant divided by the total release produced by detergent lysis of the cells. In tubes where inhibiting antibody is present, the ratio of fractional release compared with the release produced by PBMC without inhibitor is used to calculate the percentage of maximal NK release. The antibodies used to inhibit release are antibodies acid eluted from term placental microvesicles and the monoclonal antibodies produced by immunization of mice with acid treated term microvesicles. Optimal effector target cell ratios are determined in preliminary experiments so that the inhibition measured is of a high degree of NK killing of target cells.

Eluted IgG From Placenta 27 acid eluted IgG preparations from term placental microvesicles were tested for complement dependent microcytotoxicity against K562 cells to find eluates with antigenic crossreaction of the polymorphic R80K epitope between the individual placental antigen and that of K562. Two of four eluates which showed marked cytotoxicity and two which were negative were chosen to show the inhibitory activity against NK killing of K562 cells. Since the monoclonal antibodies were selected as all reacting with monomorphic sites on the R80K antigen, all would bind to K562. Monoclonals were used as controls which reacted with syncytiotrophoblast proteins other than R80K or normal IgG and IgM preparations.

Three monoclonal antibodies were found which had affinity for the R80K molecule using a solid phase enzyme immunoassay. A microvesicle preparation from a single placenta was treated with 0.1M citrate buffer at pH 3.0 and the eluted antibody and the acidified vesicles used in the assay. Tubes were coated with antimouse immunoglobulin and the individual monoclonal antibodies followed by acidified microvesicles. The eluted human IgG antibody was added and finally a peroxidase labelled anti-human IgG. Positive binding was detected of three monoclonals which bound to the R80K molecule by a different epitope than that to which the human IgG antibody was bound. The BA11 monoclonal antibody was of the IgM class and the G9 and E9 monoclonal antibodies were IgG1. These three antibody preparations were then tested for suppressive activity in four inhibition systems.

Human NK Cytotoxicity

A dose response curve for the monoclonals for the inhibition of killing $^{51}Cr$-labelled K562 cells by human peripheral blood lymphocytes (PBL) prepared with Lymphoprep from normal human blood samples. In addition a similar study was performed with the four acid eluted antibodies from human placental microvesicle preparations. Using complement dependent cytotoxicity of K562 cells, two eluates out of twenty were cytotoxic for K562. These two and two others that were not cytotoxic were tested for their ability to inhibit Nk killing of the K562 cell line. The eluated antibodies which did have specificity for K562 both showed clear dose dependent inhibition of $^{51}$Cr release by PBL, but the two others which did not bind also did not inhibit nor did they control normal IgG containing preparations (FIG. 15). All were tested in the same range of IgG concentrations. When the monoclonals were tested similarly it was found that BA11 did produce dose dependent inhibition, but the other two monoclonal antibodies did not (FIG. 16). Inhibition was not found by mouse immunoglobulin preparations nor by mouse monoclonal antibodies directed against other microvesicle antigens.

Example 5

Murine Trophoblast NK Assay

Cultured $^{51}$Cr-labelled murine cytotrophoblast cells are plated out at a concentration of $2 \times 10^4$ cells/well in flat bottomed microtiter plates. Mouse spleen NK cells (Clark et al., *Cellular Immunology* 154: 143–52 (1994)) are added at an effector target ratio of 25:1. After incubation the cells are harvested and the released label measured. Results are expressed as the percentage release of the total, the latter determined as that releasable by detergent lysis of the cells. Quadruplicate wells are used for each sample.

Mouse Resorption Experiments:

Abortion/Resorption Model

DBA/2J and Balb/k male mice and CBA/J and Balb/k females were purchased from Iffa Credo, L'Arbresle, France, and housed in a conventional breeding facility. The animals were maintained on a 12 hour light/dark cycle with food and water ad libitum. Female CBA/J mice were mated to DBA/2J males and the Balb/k females and males were mated together. The morning of sighting the vaginal plug was designated as day 0.5 of pregnancy. The mice were sacrificed on day 13.5 of pregnancy and the number of healthy and resorbing implants recorded.

Endotoxin Induced Abortion/Resorption Model

Female mice, as above are treated by intraperitoneal injection of 100 ug *E. coli* lipopolysaccharide (LPS, Sigma) on days 6.5, 8.5 and 10.5 days of pregnancy.

Sonic Stress Abortion/Resorption Model

Male DBA/2J, Balb/c and CBA/J mice were purchased from Jackson Laboratories, Bar Harbour, Maine and housed in a clean cage facility. Animal care and experiments followed institutional ethical guidelines. After overnight cohabitation of CBA/J females with DBA/2J males, those females with vaginal plugs (day 0.5 of pregnancy) were segregated and randomised to the treatment groups. One group of females were exposed to ultrasonic stress from a rodent repellent device (BRC Rongelec, France) for 24 hours beginning at 1000 hours of day 5.5 of pregnancy. Mice were killed on days 9.5, 10.5 or 13.5 of pregnancy and the total number of healthy and resorbing sites were recorded. Antibody treated mice were injected i.p. with 5 μg of hybridoma supernatant of clone BA11 on days 4.5, 5.5 and 6.5 of pregnancy.

The results for all three groups are quite remarkable. FIGS. 11, 12, 13 and 14 show that very effective suppression of abortion occurred in all three models with the murine antibody, although it was derived against a human trophoblast protein, R80K. It is thus clear that the monoclonal was able to block NK killing of K562, similarly to that found with the acid eluted human maternal alloantibody, but it was binding to a different site since the 'sandwich' assay used to detect it had the alloantibody bound to another site. It was able to block the killing of murine trophoblast by murine NK presumably because it was directed against a similar epitope on murine trophoblast. Both the alloantibodies and the BA11 antibody are expected to react with sites close to each other in order that either or both could inhibit the reaction of the NK Cell with the target molecule on the K562 cell. Acidified microvesicles were digested with trypsin and SDS PAGE of the antigen followed by Western blotting with the monoclonals showed that BA11 was on the same fragment as bound human IgG antibody, whereas the other two monoclonals reacted with smaller fragments of the R80K protein.

Figure 14:
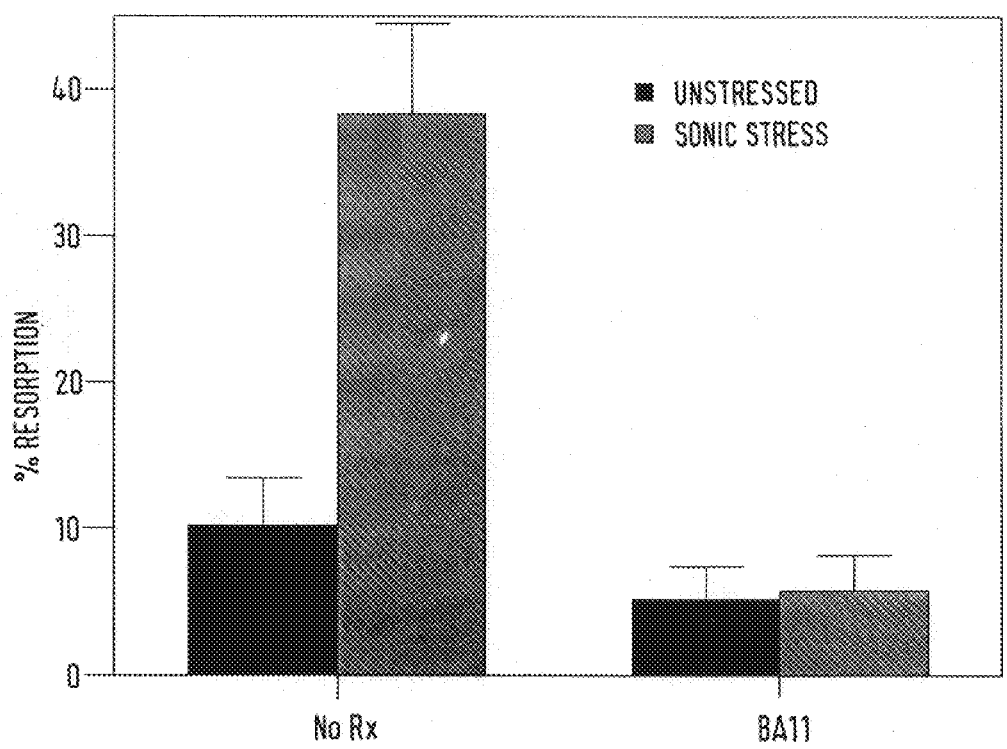
FIG. 14 demonstrates graphically the effect of BA11 in preventing resorptions due to sonic stress. Sonic stress was used to induce a high resorption rate in CBA×DBA/2 matings. Pregnant mice were injected with 10ug of BA11 or control saline on days 4.5, 5.5 and 6.5. The sonic stress elevated the resorption fraction from 14/137 implants in unstressed animals (10.2%) to 46/120 (38%). BA11 treatment reduced the resorption fraction in unstressed controls to 2/39 (5.1% 0 and to 6/105 (5.7%) in stressed animals. by Fisher's exact test p=0.0006 and p=0.0003 respectively.

In FIG. 14 the results of adding different amounts of BA11 or G9 to cultures of murine NK cells with murine trophoblast targets. Complete inhibition of NK activity occurred at a dose of 2.5 μg/well, whereas no inhibition of chromium release was found with G9. When the effector:target ratio was 100:1 BA11 reduced the percent lysis from 46.6±4.3 to 12.2±1.9 and G9 reduced lysis from 46±3.5 to 30.6±3.1. This difference is significant ($p=9.3 \times 10^{-5}$).

The results shown in Examples 4 and 5 demonstrated firstly that the antibody bound to the R80K antigen on human placenta. will, if it cross reacts with the homologous epitope on K562 cells or murine trophoblast, inhibit killing of that target. Second, one of the three monoclonals which reacted. with the human R80K protein inhibited NK killing. The other two did not have any suppressive activity, and react with a different tryptic fragment of the R80K molecule than that of the suppressive monoclonal antibody BA11.

The monoclonal antibodies have been selected as reacting with a conserved epitope on R80K, by immunization with acidified microvesicles from one placenta and screening with another. It is therefore not entirely surprising to find that three anti-R80K monoclonal antibodies also react with a homologous murine protein, although they do not detect a similar protein in the horse.

There have been suggestions that the activity of NK cells might be affected by binding to the Fcγ receptor on the peripheral blood NK cells (Sulica et al., *J. Immunol.* 126:1031–36 (1982). That the inhibition of NK killing is these studies is not by this mechanism is shown by the fact that the BA11 molecule is an IgM and the ineffective monoclonals are IgG. In addition in the endometrium, the predominant human NK cell is CD56$^+$ CD16$^-$ unlike the PBMC NK cell which is CD56$^+$ CD16$^+$.

It has been shown that the mechanism of abortion in CBAxDbA2 model is by NK killing following TNFa stimulation of NK cells and preventable with immunisation or passive transfer of antibody by depletion of the effector cells or by prevention of TNF release from macrophages with administration of pentoxyphylline (Kinsky et al. *Colloque INSERM* 212:245–59 (1991)). Similarly in the endotoxin induced model, the LPS activates macrophages to produce TNF and the NK cells in the endometrium then causes abortion. The uterine mechanism for the sonic stress induced abortion is clearly overcome by the presence of the BA11 antibody and thus there is clearly a common pathway in all three models.

What is claimed is:

1. An antibody which binds to a conserved epitope on an 80 kD single chain protein antigen present on placental surface syncytiotrophoblast and K562 cells ("R80K"), wherein said antibody inhibits NK and LAK-mediated killing of placental surface syncytiotrophoblast and K562 cells.

2. An antibody as claimed in claim 1, wherein said antibody is of class IgG or IgM.

3. An antibody as claimed in claim 2, wherein said antibody is a monoclonal antibody.

4. A hybridoma which produces a monoclonal antibody as claimed in claim 3.

5. An antibody as claimed in claim 3, wherein said antibody is a monoclonal antibody deposited at the European Collection of Animal Cell Cultures having accession number 95042013, and is designated as BA11.

6. A hybridoma which produces a monoclonal antibody as claimed in claim 5.

7. An antibody as claimed in claim 5, wherein BA11 is humanized.

8. A composition comprising an effective amount of an antibody as claimed in claim 7, in which the antibody is mixed with a suitable carrier or adjuvant.

9. A method of treating or suppressing NK induced abortion in a patient, said method comprising administering an effective amount of the composition claimed claim 8.

10. A method of making a composition comprising admixing an antibody as claimed in claim 3 with a suitable carrier or adjuvant.

11. A method of making a composition comprising admixing an antibody as claimed in claim 1 with a suitable carrier or adjuvant.

12. A composition comprising an effective amount of an antibody as claimed in claim 1, in which the antibody is mixed with a suitable carrier or adjuvant.

13. A method of treating or suppressing NK induced abortion in a patient, said method comprising administering an effective amount of the composition claimed in claim 12.

* * * * *